US006946547B2

(12) United States Patent
Rouhani et al.

(10) Patent No.: US 6,946,547 B2
(45) Date of Patent: Sep. 20, 2005

(54) ECSTASY-CLASS ANALOGS AND USE OF SAME IN DETECTION OF ECSTASY-CLASS COMPOUNDS

(75) Inventors: Riaz Rouhani, Concord, CA (US); Anthony de Jesus Sanchez, Concord, CA (US); David Davoudzadeh, Pleasanton, CA (US); William A. Coty, Fremont, CA (US); Cynthia A. Vistica, Dublin, CA (US)

(73) Assignee: Microgenics Corporation, Fremont, CA (US)

( * ) Notice: Subject to any disclaimer, the term of this patent is extended or adjusted under 35 U.S.C. 154(b) by 0 days.

(21) Appl. No.: 10/457,314

(22) Filed: Jun. 9, 2003

(65) Prior Publication Data

US 2003/0207469 A1 Nov. 6, 2003

Related U.S. Application Data

(62) Division of application No. 09/521,070, filed on Mar. 8, 2000, now abandoned.

(51) Int. Cl.$^7$ ...................... C07K 16/44; G01N 33/533; G01N 33/535
(52) U.S. Cl. ...................... 530/388.9; 435/6; 435/7.71; 435/7.93; 435/7.94; 435/7.7; 435/7.72; 436/545; 436/546; 436/525; 436/534; 530/389.8
(58) Field of Search ........................... 530/388.9, 389.8; 435/7.93, 6, 7.94, 7.7, 7.72, 7.71; 436/545, 546, 534, 525

(56) References Cited

U.S. PATENT DOCUMENTS

| | | | |
|---|---|---|---|
| 4,708,929 A | 11/1987 | Henderson ...................... 435/7 |
| 5,248,791 A | 9/1993 | Brynes et al. .............. 549/223 |
| 5,470,997 A | 11/1995 | Buechler et al. ............. 558/254 |
| 5,488,114 A | 1/1996 | Shigetoh et al. ............ 548/510 |
| 5,501,987 A | 3/1996 | Ordonez ...................... 436/534 |
| 5,618,926 A | 4/1997 | Salamone et al. .......... 530/403 |
| 5,760,184 A | 6/1998 | Swain et al. ................. 530/387 |
| 5,876,727 A | 3/1999 | Swain et al. ............. 424/193.1 |
| 5,976,812 A | 11/1999 | Huber et al. ................. 435/7.1 |
| 6,306,616 B1 | 10/2001 | Shindelman ............... 435/7.93 |

FOREIGN PATENT DOCUMENTS

| | | | |
|---|---|---|---|
| EP | 0363041 A1 | 4/1990 | |
| EP | 0371253 B1 | 6/1990 | |
| EP | 0574782 B1 | 12/1993 | |
| WO | 9610179 | 4/1996 | |
| WO | 0114371 A1 | 3/2001 | ......... C07D/405/14 |

OTHER PUBLICATIONS

Amaiz et al, *Preparation of N–heterocyclic derivatives as NOS Inhibitors*, Chemical Abstract No 129:231019 & WO 98/37079A1 (See compound with Reg. No. 212635–56–8).

Belke, J. et al., *Immunoaffinity extraction of morphine, morphine–3–glucuronide and morphine–6–glucuronide from blood of heroin victims for simultaneous high–performance liquid chromatographic determination*, Journal of Chromatography B, 726 (1999), pp. 111–119.

Bellet, Neal, *Enhanced Detection of Benzodiazepines by Immunoassay*, Journal of Analytical Toxicology, vol. 21, Jan./Feb. 1997, p. 76.

Boehringer Mannheim, *Cedia Dau Opiate*, Boehringer Mannheim, Catalog Nos. 1557386, 1661175, 1661248, May 1996, 98–695–1.

Boehringer Mannheim, *Oplate–Qualitative*, Boehringer Mannheim, Kit Catalog Nos. 1557386, 1661175, 1661248, pp. 1–15.

Chandrakumar, Nizal S. et al., *Phenylphosphonate Monoester Analogs of Cocaine, Potential Haptens for the Generation of Catalytic Antibodies*, Bioorganic & Medicinal Chemistry Letters, vol. 3, No. 2, 1993, pp. 309–312.

Charbonnier, Jean–Baptiste et al., *Crystal structure of the complex of a catalytic antibody Fab fragment with a transition state analog: Structural similarities in esterase–like catalytic antibodies*, Biochemistry, Proc. Natl. Acad. Sci. USA, vol. 92, Dec. 1995, pp. 11721–11725.

Clifton, ftp://hyperreal.com/drugs/misc/shulgin.visit, Nov. 11, 1996, pp. 1–5.

Cody, John T. et al., *Fluorescence Polarization Immunoassay Detection of Amphetamine, Methamphetamine, and Illicit Amphetamine Analogues*, Journal of Analytical Toxicology, vol. 17, Jan./Feb. 1993, pp. 26–30.

Cone, Edward J. et al., *Forensic Drug Testing for Opiates. V. Urine Testing for Heroin, Morphine, and Codeine With ommerical Opiate Immunoassays*, Journal of Analytical Toxicology, vol. 17, May/Jun. 1993, pp. 156–164.

(Continued)

Primary Examiner—Mary E. Ceperley
(74) Attorney, Agent, or Firm—Wood, Herron & Evans, L.L.P.

(57) ABSTRACT

The present invention provides a system for the improved detection of ecstasy-class compounds in biological samples. New ecstasy-class analogs are provided for detection of such ecstasy-class drugs. These analogs are compounds, or salts thereof, of a 2-amino-methylenedioxyphenyl (MDP) derivative attached to Z, where Z is a moiety capable of bonding, either directly or indirectly, with an immunogenic carrier, a detectable label, or a solid capture vehicle. Such analogs may be used to construct immunogens, enzyme or enzyme-donor conjugates, and other conjugates. The immunogens reproducibly generate antibodies with an exquisite ability to distinguish various ecstasy-class drugs in biological samples from potentially interfering substances. The specific antibodies and the conjugates may be used to distinguish and measure various ecstasy-class compounds in biological samples, such as those obtained from an individual suspected of substance abuse. In another aspect, the invention includes certain reagents, reagent combinations, and kits for performing assay methods for ecstasy-class compounds in a biological sample.

9 Claims, 1 Drawing Sheet

OTHER PUBLICATIONS

Cone, Edward J. et al., *Forensic Drug Testing For Opiates. IV. Analytical Sensitivity, Specificity, and Accuracy of Commercial Urine Opiate Immunoassays,* Journal of Analytical Toxicology, vol. 16, Mar./Apr. 1992, pp. 72–78.

Cone, Edward J. et al., *Forensic Drug Testing for Opiates: I. Detection of 6–Acetylmorphine in Urine as an Indicator of Recent Heroin Exposure: Drug and Assay Considerations and Detection Times,* Journal of Analytical Toxicology, vol. 15, Jan./Feb. 1991, pp. 1–7.

Coty, William A. et al., *CEDIA R Homogeneous Immunoassays: Current Status and Future Prospects,* Journal of Clinical Immunoassay, Ffall 1994, vol. 17, No. 3, pp. 144–150.

Derks, H.J.G.M. et al., *Determination of the Heroin Metabolite 6–Acetylmorphine by High–Performance Liquid Chromatography Using Automated Pre–Column Derivatization and Fluorescence Detection,* Journal of Chromatography, 370, 1986, pp. 173–178.

Diagnostics Reagents, Inc., *Opiate Enzyme Immunoassay,* Diagnostics Reagents, Inc., Oct. 1998, pp. 1–2.

Elliott, H.W. et al., *Actions and metabolism of heroin administered by continuous intravenous infusion to man,* Clinical Pharmacology and Therapeutics, vol. 12, No. 5, pp. 806–814.

ElSohly, Mahmoud A., *Drug Testing in the Workplace: Could a Postive Test for One of the Mandated Drugs Be for Reasons Other Than Illicit Use of the Drug?,* Journal of Analytical Toxicology, vol. 19, Oct. 1995, pp. 450–458.

Fay, John et al., *Detection of Methamphetamine in Sweat by EIA and GC–MS,* Journal of Analytical Toxicology, vol. 20, Oct. 1996, pp. 398–403.

Fehn, Josef et al., *Detection of O6–Monoacetylmorphine in Urine Samples by GC/MS as Evidence for Heroin Use,* Journal of Analytical Toxicology, vol. 9, May/Jun. 1985, pp. 134–138.

Fu et al., *Synthesis and vasodilating activity of benzamide and cinnamide derivatives,* Chemical Abstract No. 131:111148, (1999), 34(2), 109–113.

Galloway, F. Roark et al., *Methadone Conversion to EDDP during GC–MS Analysis of Urine Samples,* Journal of Analytical Toxicology, vol. 23, Nov./Dec. 1999, pp. 615–619.

George, S. et al., *A Pilot Study to Determine the Usefulness of the Urinary Excretion of Methadone and its Primary Metabolite (EDDP) as Potential Markers of Compliance in Methadone Detoxification Programs,* Journal of Analytical Toxicology, vol. 33, Mar./Apr. 1999, pp. 81–85.

Gerhards, Petra et al., *Determination of Designer Drugs and Ecstasy,* Git LaborMedizin, May 1996, pp. 212–216.

Giroud, C. et al., *2C–B: A New Psychoactive Phenylethylamine Recently Discovered in Ecstasy Tablets Sold on the Swiss Black Market,* Journal of Analytical Toxicology, vol. 22, Sep. 1998, pp. 345–354.

Glare, P.A. et al., *Clinical Pharmacokinetics of Morphine,* Therapeutic Drug Monitoring, 13, (1991), pp. 1–23.

Granquist, Lamont, *#156 TM; 4–TM; 4–Thiomescaline,* Phenethylamines I Have Known and Loved, Nov. 21, 1996, pp. 1–5.

Granquist, Lamont *#8 Arladne: 4C–DOM; BL–3912: Dimoxamine,* Phenethylamines I Have Known and Loved, Nov. 21, 1996, pp. 1–5.

Granquist, Lamont, *#157 TMA; 3,4,5–Trimethoxyamphetamine,* Phenethylamines I Have Known and Loved, Nov. 21, 1996, pp. 1–7.

Granquist, Lamont, *Quick Index to PiHKAL,* lamont@hyperreal.com, Oct. 31, 1994, pp. 1–3.

Granquist, Lamont, *#142 PEA; Phenethylamine,* Phenethylamines I Have Known and Loved, Nov. 21, 1996, pp. 1–4.

Hanisch, W. et al., *Determination of the Heroin Metabolite 6–Monoacetylmorphine in Urine by High–Performance Liquid Chromatography with Electrochemical Detection,* Journal of Analytical Toxicology, vol. 17, Jan./Feb. 1993, pp. 48–50.

Henderson, Daniel R. et al., *CEDIA, a New Homogeneous Immunoassay System,* Clinical Chemistry, vol. 32, No. 9, 1986, pp. 1637–1641.

Huestis, Marilyn A. et al., *Detection Times of Marijuana Metabolites in Urine by Immunoassay and GC–MS,* Journal of Analytical Toxicology, vol. 19, Oct. 1995, pp. 443–449.

Jenkins, Amanda J. et al., *6–Acetylmorphine Detection in Postmortem Cerebrospinal Fluid,* Journal of Analytical Toxicology, vol. 22, Mar./Apr. 1998, pp. 173–175.

Khanna, P.L. et al., *A recombinant protein–based homogeneous immunoassay,* Americal Clinical Laboratory, Oct. 1989, pp. 1–5.

Khanna, Pyare L. et al., *A new homogenous enzyme immunoassay using recombinant enzyme fragments,* Clinica Chimica Acta, 185 (1989), pp. 231–240.

Kintz, Pascal et al., *Immunassay Responses of MBDB,* Journal of Analytical Toxicology, vol. 21, Nov./Dec. 1997, pp. 589–590.

Lin, Dong–Liang et al., *Determination of Codeine, Morphine and 6–Acetylmorphine in Urine,* Journal of Food and Drug Analysis, 1996. 4(1): 25–34.

Lingenfelter, C. et al., *CEDIA EDDP (Methadone Metabolite) Assay for Urine Drug Testing,* Roche Diagnostics, Boehringer Mannheim Corporation, pp. 1–4.

Lingenfelter, C.D. et al., *A Novel Method for Elimination of Amphetamine False Positive Results During Immunoassay Screening,* The Society of Forensic Toxicologists, 1999 Annual Meeting, Oct. 1999, pp. 1–5.

Masseyeff, R.F. et al., *Reprint from Methods of Immunological Analysis,* VCH Verlagsgesellschaft mbH, 1993, pp. 416–426.

Meadway, Claire et al., *Opiate concentrations following the ingestion of poppy seed products—evidence for 'the poppy seed defense',* Forensic Science International, 96 (1998), pp. 29–38.

Meatherall, Robert C. et al., *CEDIA dau Benzodiazepine Screening Assay: A Reformulation,* Journal of Analytical Toxicology, vol. 22, Jul./Aug. 1998, pp. 270–273.

Microgenics Corporation, *Cedia DAU Opiate 2K,* Microgenics Corporation, Oct. 1998, pp. 1–4.

Miller, James J. et al., *Digoxin Immunoassay with Cross–Reactivity of Digoxin Metabolites Proportional to Their Biological Activity,* Clincial Chemistry, vol. 40, No. 10, 1994, pp. 1898–1903.

Moeller, M.R. et al., *Ecstasy and Related Substances—Serum Levels in Impaired Drivers,* Journal of Analytical Toxicology, vol. 21, Nov./Dec. 1997, p. 591.

Moellar, M.R. et al., *The detection of 6–monoacetylmorphine in urine, serum and hair by GC/MS and RIA,* Forensic Science International 70, 1995, pp. 125–133.

Mule, S. J. et al., *Rendering the "Poppy–Seed Defense" Defenseless: Identification of 6–Monoacetylmorphine in Uring by Gas Chromatography/Mass Spectroscopy,* Clinical Chemistry, vol. 34, No. 7, 1988, pp. 1427–1430.

O'Neal, Carol L. et al., *The detection of acetylcodeine and 6–acetylmorphine in opiate positive urines,* Forensic Science International, 95 (1998), pp. 1–10.

Orsulak, Paul J. et al., *Performance of the CEDIA EDDP (Methadone Metabolite) Assay,* Toxicology Laboratories, VA North Texas Health Care System, pp. 1–5.

A. Padwa et al, *Synthesis of the perhydroindolizine nucleus by a Pummerer/Mannich induced cyclization cascade,* Tetrahedron Lett., Chemical Abstract No. 130:66356 (1998), 39(47), 8585–8588.

Paul, Buddha D. et al., *Gas Chromatography/Electron Impact Mass Fragmentometric Determination of Urinary 6–Acetylmorphine, a Metabolite of Heroin,* Journal of Analytical Toxicology, vol. 13, Jan./Feb. 1989, pp. 2–7.

Poklis, Alphonse et al., *Emit–d.a.u. Monoclonal Amphetamine/Meth–Amphetamine Assay. II. Detection of Methylenedioxyamphetamine (MDA) and Methylenedioxymethamphetamine (MDMA),* Forensic Science International, 59 (1993), pp. 63–70.

Ritter, Detlef et al., *Interference with testing for lysergic acid diethylamide,* Clinical Chemistry, 43:4 (1997), pp. 635–637.

Roche Diagnostics Corporation, *Abuscreen OnLine Automated Assays for Drug Abuse, Opiates–Qualitative,* Roche Diagnostics, 1999, pp. 1–20.

Rohrich, Jorg et al., *Drogennachweis im Speichel mit dem Immunoassay Triage1)2) Detection of drugs in saliva using the immunoassay Triage,* Blutalkohol, vol. 34, 1997, pp. 102–114.

Rop, Pok Phak et al., *Determination of 6–monoacetylmorphine and morphine in plasma, whole blood and urine using high–performance liquid chromatography with electochemical detection,* Journal of Chromatography B, 661 (1994), pp. 245–253.

Ropero–Miller, Jeri D. et al., *Automated On–Line Hydrolysis of Benzodiazepines Improves Sensitivity of Urine Screening by a Homogeneous Enzyme Immunoassay,* Clinical Chemistry 43, No. 9, 1997, pp. 1659–1660.

Ruangyutikarn, Werawan et al., *Comparison of Three Commercial Amphetamine Immunoassays for Detection of Methamphetamine, Methylenedioxyamphetamine, Methylenedioxymethamphetamine, and Methylenedioxyethylamphetamine,* Journal of Analytical Toxicology, vol. 12, Jul./Aug. 1988, pp. 229–233.

Sabo, Marie et al., *A QA robotic system to perform chemical analyses,* American Laboratory, Sep. 1997, pp. 21–24.

Shindelman, J. et al., *Development and Evaluation of an Improved Method for Screening of Amphetamines,* Journal of Analytical Toxicology, vol. 23, Oct. 1999, pp. 506–510.

Shulgin, Alexander et al., *Phenethylamines I Have Known and Loved,* PiHKAL: A Chemical Love Story, Nov. 21, 1996, pp. 1–8.

Shulgin, Alexander, *The End of Psychedelic Exploration—from Slothrop Homage to: Shulgin's Psychedelic Publications,* ftp://hyperreal.com/drugs/psychedelics/misc/shulgin–bib, Nov. 21, 1996, pp. 1–8.

Singh, Jasbir, *Reagent Lot–to–Lot Variability in Sensitivity for Amphetamine with the Syva Emit II Monoclonal Amphetamine/Methamphetamine Assay,* Journal of Analytical Toxicology, vol. 21, Mar./Apr. 1997, pp. 174–175.

Smith, Dennis A. et al., *Identification of an Arylesterase as the Enzyme Hydrolysing Diacetylmorphine (Heroin) in Human Plasma,* Biochemical Pharmacology, vol. 25, Pergamon Press, 1976, pp. 367–370.

STNEasy, *Chemistry References, Search question: ecstasy AND determination,* STNEasy Session Transcript Sep. 13 12:08:50 1999, pp. 1–22.

Titmas, Richard C. et al., *Aspects of Antibody–Catalyzed Primary Amide Hydrolysis,* Applied Biochemistry and Biotechnology, vol. 47, 1994, pp. 277–292.

F. Uckun et al, *N'–[2–(2–thiophene)ethyl]–N'–[2–(5–bromopyridyl)] thiourea as a potent inhibitor of NNI–resistant and multidrug–resistant human immunodeficiency virus–1,* Chemical Abstract No. 132:146216, Boiorg.Med.Chem. Lett., (1999), 9(24), 3411–3418.

Examiner Dr. William Thomson, *United Kingdom Search Report,* Date of Search: Aug. 3, 2001.

Vaughan, Brent, *Multiconstituent calibrators for recombinant–based TDM assays,* American Clinical Laboratory, May 1997, pp. 1–2.

Verstraete, Alain et al., *Evaluation of the Diagnostica Performance of the Boehringer Mannheim CEDIA LSD Assay,* Journal of Analytical Toxicology, vol. 22, No. 7, Nov./Dec. 1998, pp. 601–603.

Wang et al, *Studies on antiarrhythmic agents II. Synthesis of 1–phenyl–3–alkylamino–1,2–propanediol analogs and screening for their antiarrhythmic activity,* Chemical Abstract No. 127:135598. (1995), 5(1), 1–5.

Weitz, Charles J. et al., *6–Acetylmorphine: A natural product present in mammalian brain,* Neurobiology, Proc. Natl. Acad. Sci., USA, vol. 85, Jul. 1988, pp. 5335–5338.

Wu, Alan H.B. et al., *CEDIA for Screening Drugs of Abuse in Urine and the Effect of Adulterants,* Journal of Forensic Sciences, JFSCA, vol. 40, No. 4, Jul. 1995, pp. 614–618.

Lind, Peter Thomas et al., *Thiourea derivatives and methods for inhibition of HIV and related viruses,* Chemical Abstract No. 119:160110, PCT Application., 550 pg.

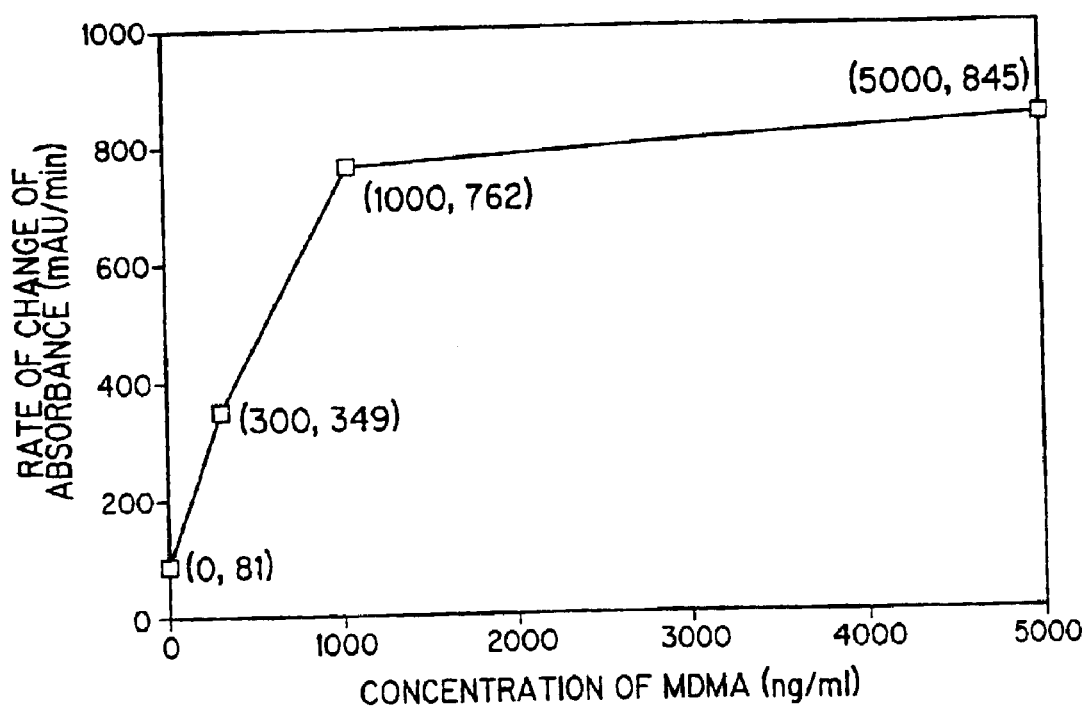

US 6,946,547 B2

ECSTASY-CLASS ANALOGS AND USE OF SAME IN DETECTION OF ECSTASY-CLASS COMPOUNDS

This application is a Divisional application of U.S. patent application Ser. No. 09/521,070 filed Mar. 8, 2000, now abandoned.

BACKGROUND OF THE INVENTION

This invention relates generally to the field of determining drugs of abuse in biological samples. More specifically, it provides a system of derivatives, conjugates and specific antibodies which may be used in assay systems for detection or quantitation of 3,4-methylenedioxymethamphetamine (MDMA), also known as ecstasy, and other related compounds.

Designer drugs are specific derivatives of commonly encountered drugs of abuse which are popular within some geographic regions and populations. Use of designer drugs carries all of the risks involved in use of more common drugs, as well as additional risks, in that detection and subsequent treatment is complicated by designer drugs' relative uniqueness. For example, some emergency facilities may not be able to detect designer drugs because such facilities lack the sophisticated and expensive instrumentation, such as gas chromatography/mass spectroscopy (GC/MS) equipment, used in confirming a positive result. Rapid screening methods such as immunoassays are more widely available, easy to use, and economical, but commonly detect only a single one of, or at most, a limited number of, the most commonly encountered drugs. Thus, they are not specific for a larger class of designer drugs.

One such class of designer drugs is the ecstasy class. Non-limiting examples of compounds in this class include, 3,4-methylenedioxymethamphetamine (MDMA), also known as "ecstasy", 3,4-methylenedioxyamphetamine (MDA), N-ethyl-3,4-methylenedioxyamphetamine (MDE) N-methyl-1-(3,4-methylenedioxyphenyl)-2-butanamine (MBDB), 1-(3,4-methylenedioxyphenyl)-2-butanamine (BDB) and other derivatives of amphetamine. In fact, as drug designers develop more and more variants of ecstasy, the number of unique compounds which falls within the ecstasy class continues to grow.

Detection of MDMA, MDA, MDE, MBDB, BDB, another ecstasy-class compound, or a derivative or metabolite thereof, in the urine currently depends upon cross-reactivity of such ecstasy-class drugs in immunoassays for amphetamine and methamphetamine. These assays, however, fail to detect such ecstasy-class compounds at lower concentrations. Moreover, existing immunoassays for amphetamine and methamphetamine are limited by their cross-reactivity to over-the-counter allergy and cold medications, such as (±) ephedrine, (+) pseudoephedrine, and phenylpropanolamine, and to prescription diet drugs such as phentermine. This cross-reactivity factor prevents one from lowering the cut-off level for detection of amphetamine and methamphetamine, which, in turn, prevents detecting ecstasy-class compounds at lower concentrations. Therefore, an assay with increased specificity for ecstasy-class compounds is needed, either as an assay to detect ecstasy-class compounds alone, or as an assay to detect ecstasy-class compounds as well as amphetamine and methamphetamine.

SUMMARY OF THE INVENTION

The present invention provides a system for the improved detection of ecstasy-class compounds in biological samples. As used herein, the terms "ecstasy-class" and "ecstasy class" are used to refer to a class of compounds, which includes, without limitation, 3,4-methylenedioxymethamphetamine (MDMA), 3,4-methylenedixoyamphetamine (MDA), N-ethyl-3,4-methylenedioxyamphetamine (MDE), N-methyl-1-(3,4-methylenedioxyphenyl)-2-butanamine (MBDB), and 1-(3,4-methylenedioxyphenyl)-2-butanamine (BDB). As will be appreciated by those of ordinary skill in the art, the ecstasy class is a constantly growing class of drugs, in that drug designers continue to synthesize new, unique compounds which, by virtue of their structure and/or psychedelic properties, fall within the ecstasy class. Accordingly, "ecstasy-class" and "ecstasy class", as used herein, include compounds which have been synthesized, as well as those which have yet to be synthesized.

One aspect of the invention is directed to ecstasy-class analogs. These analogs are capable of being used to construct immunogens, antibodies, enzyme or enzyme-donor conjugates, and other conjugates.

The immunogens reproducibly generate antibodies with an exquisite ability to distinguish various ecstasy-class drugs in biological samples from potentially interfering substances. The specific antibodies and conjugates may be used to distinguish and measure various ecstasy-class compounds in biological samples, such as those obtained from individuals suspected of substance abuse. Another aspect of the invention relates to certain reagents, reagent combinations, and kits for performing assay methods for ecstasy-class compounds in a biological sample.

With regard to the ecstasy-class analogs, one aspect of the invention is directed to a compound, or a salt thereof, wherein the compound is a 2-amino-methylenedioxyphenyl (MDP) derivative attached to Z, where Z is a moiety capable of bonding, either directly or indirectly, with an immunogenic carrier, a detectable label, or a solid capture vehicle.

Another aspect is directed to a compound, or a salt thereof, in which the compound has the following structure:

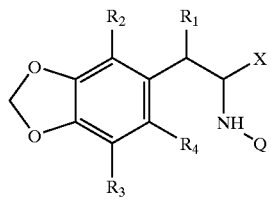

or a salt thereof, wherein X, Q, $R_1$, $R_2$, $R_3$, and $R_4$ independently are selected from the group consisting of hydrogen, a first moiety, a substituted derivative of the first moiety, and $L^1_n$—Z, with the proviso that at least one of X, Q, $R_1$, $R_2$, $R_3$, and $R_4$ is $L^1_n$—Z;

where the first moiety is selected from the group consisting of a straight moiety, a branched moiety, a cyclic moiety, and combinations thereof, and the first moiety has a backbone of m backbone atoms where m is an integer $\geq 1$, with the m backbone atoms independently selected from the group consisting of carbon, nitrogen, oxygen, sulfur, a non-substitutable halide, and combinations thereof;

where $L^1_n$ is selected from the group consisting of a second moiety and a substituted derivative of the second moiety;

where the second moiety is selected from the group consisting of a straight moiety, a branched moiety, a cyclic moiety, and combinations thereof, and the second moiety has a backbone of n backbone atoms where n is an integer≧0, with the n backbone atoms independently selected from the group consisting of carbon, nitrogen, oxygen, sulfur, a non-substitutable halide, and combinations thereof; and where Z is a moiety capable of chemically bonding, either directly or indirectly, with an immunogenic carrier, a detectable label, or a solid capture vehicle.

The detectable label of the invention may be any suitable label, as will be appreciated by one of ordinary skill upon reading this specification. For example, the detectable label may be a radioisotope, a fluorescent group, a fluorescence quenching group, a phosphorescent group, a chemiluminescent group, a chromophoric group, a chromogenic substance, a pigment, a dye, an electrochemically active group, an electrochemiluminescent group, a group that undergoes a change in fluorescence, phosphorescence, chemiluminescence or electrochemical property upon binding, a peptide, a protein, a protein fragment, an immunogenic carrier, an enzyme, an enzyme inhibitor, an enzyme substrate, an enzyme cofactor, an enzyme prosthetic group, an enzyme donor, a solid particle, a magnetic particle, an insoluble particle, a latex particle, a gold particle, a solid surface, an antibody, a nucleic acid, or a suitable combination of such detectable labels.

The immunogenic carrier may be any suitable material capable of bonding, directly or indirectly, with the Z moiety of a Z-containing compound (e.g., an ecstasy-class analog) of the invention to produce an immunogen, as will be appreciated by those of ordinary skill in the art. The solid capture vehicle of the invention may be a solid particle, a solid surface, or a combination thereof. By way of example, the solid particle may be a magnetic particle, an insoluble particle, a latex particle, or a gold particle. Also by way of example, the solid surface may be a slide or a microtiter plate.

The invention also encompasses a method of obtaining an antibody specific for ecstasy-class compounds, with the method comprising immunizing an animal or contacting an immunocompetent cell or virus with an immunogenic ecstasy-class analog conjugate of this invention. The animal may be a vertebrate, for example, a mammal. The antibodies may be in soluble form, or may be insolubilized by attachment to a solid capture vehicle, such as a solid surface, solid support, solid particle, or insoluble particle, for example.

Yet another aspect of the invention is an antibody specific for ecstasy-class compounds, and having a cross-reactivity with potentially interfering substances below a certain threshold. For example, the antibody may have a cross-reactivity with each of ephedrine, pseudoephedrine, and phenylpropanolamine of less than 10%, advantageously less than 1%, and more advantageously less than 0.1%. Alternatively, or additionally, the antibody may have a cross-reactivity with each of amphetamine, methamphetamine, and 4-hydroxy-3-methoxymethamphetamine (HMMA) of less than about 1%. Also embodied in the invention are reagent sets and reagent systems comprised of an antibody specific for ecstasy-class compounds and labeled ecstasy-class analogs or ecstasy-class analog conjugates that can be used in combination to conduct an immunoassay for ecstasy-class compounds. Thus, the invention also encompasses immunoassay reagents comprising a protein or peptide conjugate of an ecstasy-class analog of the invention, where the protein or peptide is an enzyme that undergoes a change in enzyme activity upon binding of the conjugate to an antibody specific for the ecstasy-class of compounds; or the protein or peptide is an enzyme donor, where the ability of the enzyme donor to complement with an enzyme acceptor to form an active enzyme complex is affected by binding of the conjugate to an antibody specific for the ecstasy-class of compounds.

Further embodiments of the invention include immunoassay methods for determining ecstasy-class compounds in a sample. One such method comprises the steps of combining the sample with an antibody specific for ecstasy-class compounds under conditions that permit formation of a stable ecstasy-class compound-antibody complex and detecting or quantitating any ecstasy-class compound-antibody complex formed. Additional steps can include contacting the antibody with a labeled ecstasy-class compound or ecstasy-class analog under conditions that permit formation of a stable complex between the labeled compound and the antibody, separating any labeled compound not forming a stable complex, and measuring the complexed or separated label as a measure of ecstasy-class compound(s) in the sample. Alternatively, the additional steps can include: contacting the antibody with an enzyme or enzyme-donor conjugate of an ecstasy-class analog under conditions that permit formation of a stable complex between the conjugate and the antibody; and measuring enzymatic activity or enzyme complementation as a measure of ecstasy-class compound(s) in the sample. Both separation and homogeneous assay methods are included in the invention.

The foregoing embodiments of this invention can be constructed as immunoassay methods to detect ecstasy-class compounds alone. Alternatively, the ecstasy-class compound-specific antibody and labeled ecstasy-class analog can be combined with similar reagents designed to detect amphetamine and methamphetamine, resulting in an amphetamines assay which exhibits greater sensitivity of detection of the ecstasy-class designer amphetamines (i.e., the ecstasy-class compounds).

Further embodiments of the immunoassay methods of the invention are a method for determining ecstasy-class compounds in a sample by incubating a reagent mixture comprising the sample, an antibody specific for ecstasy-class compounds, and a labeled ecstasy-class analog of the invention under conditions that permit formation of a stable complex between the antibody and any ecstasy-class compound(s) in the sample, and detecting or quantitating fluorescence, phosphorescence, chemiluminescence, electrochemiluminescence, electrochemical property, or any change in these properties, as a measure of ecstasy-class compounds in the sample. An ecstasy-class analog conjugated to an enzyme or enzyme donor can also be used in this method, with the mixture also comprising a substrate for the enzyme and, if an enzyme-donor conjugate is used, an enzyme acceptor for the enzyme donor, where detecting or quantitating the enzymatic conversion of the substrate to a product is a measure of ecstasy-class compounds in the sample. A suitable enzyme is beta-galactosidase; when an enzyme-donor/enzyme-acceptor combination is used, a beneficial enzyme-donor/enzyme-acceptor complex is one that has beta-galactosidase activity.

The invention also encompasses a method for enriching ecstasy-class compounds from a biological sample, comprising incubating the sample with an antibody specific for ecstasy-class compounds under conditions that permit binding of the antibody to any ecstasy-class compounds in the sample to form a complex, and separating complex that has formed from other components of the sample. The antibody may be bound to a solid capture vehicle (for example, solid support, solid surface, solid particle, or insoluble particle), in which case separation of the insolubilized antibody-ecstasyclass compound complex is followed by washing the insolubilized complex, then by elution of the material bound to the antibody. After the solution has been enriched in ecstasy-class compound(s), it can be assayed for any ecstasy-class compound(s) obtained.

BRIEF DESCRIPTION OF THE DRAWING

The FIGURE is a graph of an ecstacy-class compound standard curve.

DETAILED DESCRIPTION OF PREFERRED EMBODIMENTS

Each of the documents (patents, patent applications, journal articles, texts, other publications, etc.) cited below, in this Detailed Description, is hereby incorporated in its entirety by reference.

The present invention is focused in part on the design and production of ecstasy-class analogs, which can then be used for preparing immunogens and conjugates useful in immunoassays for the determination of ecstasy-class compounds. The ecstasy-class analogs are represented by compounds, or salts thereof, where the compounds are the combination of a 2-amino-methylenedioxyphenyl (MDP) derivative and Z, wherein Z is a moiety capable of bonding, either directly or indirectly, with an immunogenic carrier, a detectable label, or a solid capture vehicle.

One such ecstasy-class analog may be represented by the following structure:

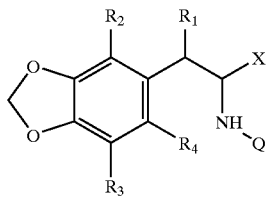

or a salt thereof,
wherein X, Q, $R_1$, $R_2$, $R_3$, and $R_4$ independently are selected from the group consisting of hydrogen, a first moiety, a substituted derivative of the first moiety, and $L^1{}_n$—Z, with the proviso that at least one of X, Q, $R_1$, $R_2$, $R_3$, and $R_4$ is $L^1{}_n$—Z;

where the first moiety is selected from the group consisting of a straight moiety, a branched moiety, a cyclic moiety, and combinations thereof, and the first moiety has a backbone of m backbone atoms where m is an integer $\geq 1$, with the m backbone atoms independently selected from the group consisting of carbon, nitrogen, oxygen, sulfur, a non-substitutable halide, and combinations thereof;

where $L^1{}_n$ is selected from the group consisting of a second moiety and a substituted derivative of the second moiety;

where the second moiety is selected from the group consisting of a straight moiety, a branched moiety, a cyclic moiety, and combinations thereof, and the second moiety has a backbone of n backbone atoms where n is an integer $\geq 0$, with the n backbone atoms independently selected from the group consisting of carbon, nitrogen, oxygen, sulfur, a non-substitutable halide, and combinations thereof; and where Z is a moiety capable of chemically bonding, either directly or indirectly, with an immunogenic carrier, a detectable label, or a solid capture vehicle.

The ecstasy-class analogs (also referred to herein as "analogs" or "analog") of this invention can either be used in the form shown, or, for example, as an internal standard or competitive binding compound in an assay system. They can also be adapted further. For example, they can be insolubilized by covalent attachment to a solid surface or insoluble particle, as described further on in this disclosure. Alternatively, they can be adapted for use in an assay system by covalently attaching a label, either directly, or through a covalent linking group. Suitable labels include radioisotopes such as $^{125}$I, a fluorescent group, a fluorescence quenching group, a phosphorescent group, a chemiluminescent group, an electrochemically active group, an electrochemiluminescent group, any group that undergoes a change in fluorescence, phosphorescence, chemiluminescence or electrochemical property upon binding, an enzyme or enzyme donor, an enzyme inhibitor, an enzyme substrate, an enzyme cofactor, and an enzyme prosthetic group. The analogs can be attached to latex particles for use in agglutination reactions; the latex particles can be opaque or contain a fluorophore or dye. The analogs can also be attached to colloidal gold. Examples of these assays are described in U.S. Pat. Nos. 5,120,643 and 5,334,538, and in Price and Newman, "Light Scattering Immunoassay," Principles and Practice of Immunoassay, (Price and Newman, eds.) New York: Stockton Press, 1991, pages 446–481.

Derivatization with aminomethylfluorescein is taught in U.S. Pat. No. 4,614,823. Enzyme and enzyme donors are described in the assay descriptions that follow. The analogs can also be adapted as immunogens by conjugating to an immunogenic substance, exemplified by proteins such as keyhole limpet hemocyanin (KLH).

"Poly(amino acids)", "proteins", "peptides", and "polypeptides" are terms used interchangeably herein to describe polymers of amino acids of any sequence, typically at least 5 amino-acids in length, linked by peptide bonds. Some examples include proteins that can be used as immunogenic carriers, and proteins that provide a detectable signal for assay purposes, for example, enzymes and enzyme donor polypeptides.

Conjugates between analogs and any type of protein or peptide, such as an enzyme, enzyme fragment, or immunogenic protein, can be prepared using any suitable linking chemistry. The reader is referred generally to Hermanson, G. T., "Bioconjugate Techniques", Academic Press: New York, 1996; and "Chemistry of Protein Conjugation and Cross-linking" by, S. S. Wong, CRC Press, 1993.

Although the invention is not so limited, it is convenient to attach proteins and other substituents by way of the 2-amino nitrogen in the analog. A functional spacer can be introduced, which will allow accessibility to the derivative once conjugated.

The phrase "a linker containing at least one carbon atom" is meant to refer to any generic linking group between two other groups, e.g., a linker between hapten and protein, or a linker between hapten and a functional group suitable for attachment to another molecule, which contains at least one carbon atom. The linker group may be a $C_1$–$C_{20}$ hydrocarbon chain containing zero to ten heteroatoms selected from the group consisting of N, O, and S, and which contains at least as many carbon atoms as heteroatoms. Examples of such generic linking groups include, but are not limited to, —O—$(CH_2CH_2O)_n$—, where n is an integer between 1 and 10 (i.e., a polyethylene glycol linker); —$CH_2CH_2$-phenyl-$CH_2CH_2$— (in ortho, meta, or para connection); —$CH_2CH_2$—CONH—$CH_2CH_2$— (i.e., an amide linkage), —C(=O)—CHS—NH— (i.e., an amino acid linker, where S is a naturally or non-naturally occurring amino acid side chain) or indeed, any straight-chain, branched, cyclic, or combination of straight-chain, branched, or cyclic linking group that will serve as a covalent linkage between the two other groups. A further example is $C_1$–$C_{20}$ alkyl groups.

Analog-protein conjugates are typically prepared by synthesizing the analog with a protein-reactive group, incubating the modified derivative with the protein under conditions that permit the conjugation reaction to occur, and then separating out the conjugate. For example, a protein conjugate can be prepared by combining an excess of a maleimide adduct with a protein having free thiol groups. Free sulfhydryls may be provided in the form of free cysteine residues or by reducing protein disulfide bonds by a reagent such as dithiothreitol. Alternatively, thiol groups can be added to a protein having free primary amino groups by reacting with 2-iminothiolane (IT) in aqueous buffer, followed by removal of unreacted IT. A detailed protocol for the thiolation of the protein KLH is provided in U.S. Pat. No. 5,439,798.

For the purposes of obtaining specific antibodies against ecstasy-class analogs, an analog-protein conjugate of this invention may comprise a plurality of analogs covalently bonded to an immunogenic protein carrier selected for its ability to provide a general immunostimulatory effect. Various protein carriers may be employed, including serum albumin, serum globulins, ocular lens proteins, lipoproteins, ovalbumin, throxine binding globulin, and synthetic polypeptides. If desired, KLH may be used.

The term "antibody" as used in this disclosure refers to both polyclonal and monoclonal antibodies and related antigen recognition units. The ambit of the term deliberately encompasses not only intact immunoglobulin molecules, but also such fragments and derivatives of immunoglobulin molecules as may be prepared by techniques known in the art, and retaining the antibody activity of an intact immunoglobulin. In this context, "antibody activity" refers to the ability of an antibody to bind a specific antigen in preference to other potential antigens via the antigen combining site located within a variable region of an immunoglobulin. Fragments and other derivatives of immunoglobulins can be prepared by methods of standard protein chemistry, such as subjecting the antibody to cleavage with a proteolytic enzyme like pepsin, papain, or trypsin, and reducing disulfide bonds with such reagents as dithiothritol. Genetically engineered variants of intact immunoglobulin can be produced by obtaining a polynucleotide encoding the antibody, and applying the general methods of molecular biology to splice encoding sequences or introduce mutations and translate the variant. Examples of engineered antibody variants include chimeric and humanized antibodies, Fab-like fragments, single-chain variable region fragments (scFv), and diabodies.

For general techniques used in raising, purifying and modifying antibodies, and the design and execution of immunoassays, the reader is referred to *Handbook of Experimental Immunology* (D. M. Weir & C. C. Blackwell, eds.); CURRENT PROTOCOLS IN IMMUNOLOGY (J. E. Coligan et al., eds., 1991); David Wild, ed., *The Immunoassay Handbook* (Stockton Press NY, 1994); and R. Masseyeff, W. H. Albert, and N. A. Staines, eds., *Methods of Immunological Analysis* (Weinheim: VHC Verlags gesellschaft mbH, 1993).

Polyclonal antibodies of this invention are raised by administration of the immunogenic analog-protein conjugate to an animal host, usually mixed with an adjuvant. Any animal host which produces antibodies can be used, with one example being a vertebrate, such as a mammal. The immunogen is conveniently prepared for injection by rehydrating lyophilized immunogen to form a solution or suspension. Exemplary adjuvants are water-in-oil immersions, for example, Freund's complete adjuvant for the first administration, and Freund's incomplete adjuvant for booster doses. The preparation is typically administered in a variety of sites, and typically in two or more doses over a course of at least 4 weeks. Serum is harvested and tested for the presence of ecstasy-class-compound antibody using an ecstasy-class-compound/protein conjugate or analog in a standard immunoassay or precipitation reaction.

Polyclonal antisera will typically contain antibodies not reactive with an ecstasy-class compound, as well as anti-ecstasy-class-compound antibodies cross-reactive with other substances including amphetamine, methamphetamine, and HMMA. Methods for purifying specific antibodies from a polyclonal antiserum are known in the art. One such method is affinity purification using a column of an ecstasy-class compound conjugated to a solid phase. One manner of preparing an ecstasy-class-compound column is to conjugate an ecstasy-class compound or an analog of this invention to a protein other than the protein used in the immunogen, and then attach the conjugate to a commercially available activated resin, such as CNBr-activated SEPHAROSE™. The anti-ecstasy-class compound is passed over the column, the column is washed, and the antibody is eluted with a mild denaturing buffer such as 0.1 M glycine, 0.2 M NaCL, pH 2.5.

Monoclonal antibodies of this invention can be prepared by a number of different techniques known in the art. For hybridoma technology, the reader is referred generally to Harrow & lane (1988), U.S. Pat. Nos. 4,491,632, 4,472, 500, and 4,444,887, and *Methods in Enzymology*, 73B:3 (1981). The most common way to produce monoclonal antibodies is to immortalize and clone a splenocyte or other antibody-producing cell recovered from an animal that has been immunized against an ecstasy-class compound as described earlier. The clone is immortalized by a procedure such as fusion with a non-producing myeloma, by transfecting with Epstein Barr Virus, or transforming with oncogenic DNA. The treated cells are cloned and cultured, and clones are selected that produce antibody of the desired specificity. Specificity testing is performed on culture supernatants by a number of techniques, such as using the immunizing antigen as the detecting reagent in an immunoassay. A supply of monoclonal antibody from the selected clone can then be purified from a large volume of culture supernatant, or from the ascites fluid of suitably prepared host animals injected with the clone. The antibody may be tested for activity as raw supernatant or ascites, and is optionally purified using standard biochemical preparation techniques such as ammonium sulfate precipitation, ion exchange chromatography, and gel filtration chromatography.

Alternative methods for obtaining antibodies involve contacting an immunocompetent cell or viral particle with an analog-protein complex of this invention in vitro. In this context, "immunocompetent" means that the cell or particle is capable of expressing an antibody specific for the antigen without further genetic rearrangement, and can be selected from a cell mixture by presentation of the antigen. Immunocompetent eukaryotic cells can be harvested from an immunized mammalian donor, or they can be harvested from an unimmunized donor and prestimulated in vitro by culturing in the presence of immunogen and immunostimulatory growth factors. Cells of the desired specificity can be selected by contacting with the immunogen under culture conditions that result in proliferation of specific clones but not non-specific clones. Immunocompetent phage may be constructed to express immunoglobulin variable region segments on their surface. See Marks et al., New Engl. J. Med. 335:730, 1996; WO patent applications 94/13804, 92/01047, and 90/02809; and McGuinness et al., Nature Biotechnol. 14:1149,1996. Phage of the desired specificity may be selected, for example, by adherence to an ecstasy-class-compound/protein complex attached to a solid phase, and then amplified in *E. coli.*

Antibodies obtained using any of the aforementioned techniques are screened or purified not only for their ability to react with an ecstasy-class compound, but also for a low cross-reactivity with potential interfering substances. "Cross reactivity" is determined in a quantitative immunoassay by establishing a standard curve using known dilutions of the target analyte, e.g., MDMA. The standard curve is then used to calculate the apparent concentration of the interfering substance present in various known amounts in samples assayed under similar conditions. The cross-reactivity is the apparent concentration divided by the actual concentration multiplied by 100. One immunoassay for determining cross-reactivity is a CEDIA® type assay using an ED28-(MD-MDA)$_2$ donor polypeptide, described in detail in Example 10. Alternatively, the cross-reactivity can be determined in the same type of immunoassay in which the antibody will ultimately be used.

It is generally worth screening antibodies for cross-reactivity with other pharmaceutical compounds that subjects may be taking collaterally, particularly those eliminated in urine and having a structure with some resemblance to ecstasy-class compounds. Of particular concern are over-the-counter allergy and cold medications, such as (±) ephedrine, (+) pseudoephedrine, and phenylpropanolamine. Additionally, if the ecstasy-class-specific reagents are to be used in combination with reagents for detection of amphetamine and methamphetamine, low cross-reactivity toward these over-the-counter allergy and cold medications is desirable in order to reduce interaction between the various reagents, and thus, to simplify assay design and formulation.

Antibodies to ecstasy-class compounds according to this invention are useful for detection of ecstasy-class compounds and for purifying ecstasy-class compounds from a mixture. Purification of ecstasy-class compounds using antibody in immunoaffinity techniques is useful in isolating preparative amounts of ecstasy-class compounds from contaminants that copurify by other techniques. Purification of ecstasy-class compounds from clinical samples in trace amounts is desirable where the samples potentially contain a substance that is not an ecstasy-class compound but may complicate readings in the detection system. For example, GC/MS tests generally require extraction of analyte from the aqueous sample. Standard liquid or solid phase extraction can give high background signals and poor sensitivity of detection. Analyte-specific immunoadsorption improves the extent of selection and also concentrates the analyte into a smaller volume than the original sample.

Potential methods of immunoaffinity purification include double antibody precipitation, protein A precipitation, and the formation of other types of antibody conjugates. One such method is solid-phase adsorption. The antibody is attached to any suitable resin, the original sample is contacted with the resin, the resin is washed, and the sample is eluted. Exemplary resins include: Sepharose® (Pharmacia), Poros® resins (Roche Molecular Biochemicals, Indianapolis), Actigel Superflow™ resins (Sterogene Bio-separations Inc., Carlsbad Calif.), and Dynabeads™ (Dynal Inc., Lake Success, N.Y.).

A coupling procedure is as follows: the required amount of activated Sepharose® is weighed, taking into account the desired coupling ratio and the fact that 1 g freeze-dried material swells to 3.5 mL gel volume. The gel is reconstituted and washed in wash buffer (1 mM HCl) (3 mL and then 200 mL per gram), and then washed in coupling buffer (0.1 M NaHCO$_3$, 0.5 M NaCl, pH 8.3) (50 mL per gram) using a Buchner funnel. The antibody is dissolved or exchanged into coupling buffer, and 5–10 mg are coupled per mL. The gel cake is transferred to a suitable sized container, the antibody is added, and the volume is adjusted to make a 50% slurry. The suspension is mixed end-over-end for 2 h at room temperature, or overnight at 2° C. to 8° C. (stirring is avoided to prevent shearing of the beads). The proportion of antibody successfully coupled is determined by measuring A$_{280}$ before and after coupling. Blocking buffer is then added (1 methanolamine pH 8.0, or 0.2 M Tris buffer, pH 8.0), and the suspension is mixed end-over-end for a further 2 h at room temperature, or overnight at 2° C. to 8° C. The gel is washed in a Buchner funnel with coupling buffer, second wash buffer (0.1 M acetate, 0.5 M NaCl, pH 4.0), and then coupling buffer (100 mL each per gram). The affinity resin can then be diluted with prepared inactivated Sepharose® 4B to yield the desired binding capacity.

Resins of this kind are typically preserved in refrigerated conditions or in the presence of a preservative such as 0.1% sodium azide. Separation may be conducted by column chromatography or batch elution. In a typical separation procedure, 10 mL of a sample being testing for the presence of an ecstasy-class compound (such as a urine sample from a human subject) is combined with 200 μL of a 50% slurry of the anti-ecstasy-class-compound resin. The reaction and extraction can be conveniently carried out in a conical sample container with a 10 mL capped reservoir fitted at the bottom with a frit and a plugged tip. A small amount buffer may also be added to the sample if the antibody is sensitive to pH variation between samples. The mixture is then capped and the resin is kept suspended for about 30 to 120 min on a platform rocking mixer or rotator. The resin is separated from the sample (for example, by filtration or centrifugation), and washed with 10 mL of phosphate-buffered saline, and twice with water. After the final wash, the resin is dried by applying a vacuum for 2–5 seconds. One mL methanol is then added, the resin is incubated for ~2–5 min, and the methanol is recovered. The methanol eluate can then be characterized for the presence of ecstasy-class compounds, which correlate with the presence of ecstasy-class compounds in the original sample. Successful elution can be confirmed by running parallel extractions on samples containing standard amounts of an ecstasy-class compound, or by including an internal standard in the sample, such as a cross-reactive substance or a stable isotope-labeled internal standard. Ecstasy-class analogs suitable for this purpose are described earlier in this disclosure.

Embodied in this invention are immunoassay methods for the presence of ecstasy-class compounds in a sample of interest, including but not limited to bodily fluids from subjects suspected of having taken MDMA ("ecstasy") or a related drug, for example, bodily fluids from humans. Suitable samples include biological samples taken from subjects, optionally diluted or modified to facilitate the assay, experimental samples generated by any chemical or biological method, and standards containing known concentrations of a particular ecstasy-class compound or other substance(s) used for assay calibration.

If desired, liquid biological samples may include urine, serum, plasma, and fluids taken during autopsy (such as cerebrospinal fluid). Tissue samples can be extracted into liquid medium for immunoassay. Hair samples can also be tested by extracting into a liquid medium. For example, hair can be washed in air and acetone to remove oils, dried, and then pulverized in a ball mill. 20–30 mg powdered hair are then incubated in a neutral buffer for about 5 h at 40° C. Also suitable are postmortem cerebrospinal fluid or vitreous humor. Sweat samples can be obtained using, for example, a PharmChek sweat patch (Sudormed, Santa Ana, Calif.), comprising a semi-occlusive dressing consisting of a medical grade cellulose blotter paper collection pad, covered by a thin layer of polyurethane and acrylate adhesives. At the end of the wear period, the pad is eluted with a suitable buffer, such as 2.5 mL of 0.2 M acetate buffer with methanol at pH 5.0 (25:75) (Fogerson et al., J. Anal. Toxicol. 21: 451, 1997), or with acetonitrile.

In most instances, the assays will involve using an antibody raised against an analog/protein conjugate of this invention, or having the characteristics of such an antibody.

The procedure entails combining the sample with the antibody under conditions that permit the formation of a stable complex between the substance to be tested (described herein as the "analyte", and typically a particular ecstasy-class compound), and the antibody. This is followed by detecting any ecstasy-class-compound/antibody complex that is formed. A "stable complex" is a complex between antibody and analyte (typically non-covalently associated) that persists at least as long as it takes the presence of the complex to be measured by the intended method.

Assays of this invention include both qualitative and quantitative assays. Typical quantitative methods involve mixing the analyte with a pre-determined amount of the reagent antibody, and correlating the amount of complex formed with the amount of analyte in the original sample using a relationship determined using standard samples containing known amounts of analyte in the range expected for the sample to be tested. In a qualitative assay, sufficient complex above or below a threshold level established by samples known to contain or be free of analyte establish the assay result. Unless otherwise stated, the act of "measuring" or "determining", as used in this disclosure, refers both to qualitative and to quantitative determination.

Assays of this invention include both separation-based and homogeneous assays. In separation based assays, the detecting of the complex involves a process wherein the complex formed is physically separated from either unreacted analyte, unreacted antibody, or both. See, e.g., U.S. Pat. No. 3,646,346. The complex may be first formed in the fluid phase, and then subsequently captured by a solid phase reagent or separated on the basis of an altered physical or chemical property, such as by gel filtration or precipitation. Alternatively, one of the reagents may be attached to a solid phase before contacting with other reagents, and then the complex may be recovered by washing the solid phase free of unreacted reagents. Separation-based assays typically involve use of a labeled analog or antibody to facilitate detection or quantitation of the complex. Suitable labels are radioisotopes such as $^{125}I$ enzymes such as peroxidase and beta-galactosidase, and fluorescent labels such as fluorescein isothiocyanate. The separation step involves removing labeled reagent present in complex form from the unreacted labeled reagent. The amount of label in the complex can be measured directly or inferred from the amount left unreacted.

In homogeneous assays, the complex is typically not separated from unreacted reaction components, but instead the presence of the complex is detected by a property which at least one of the reactants acquires or loses as a result of being incorporated into the complex. Homogeneous assays known in the art include systems involving: fluorochrome and fluorochrome quenching pairs on different reagents (U.S. Pat. Nos. 3,996,345; 4,161,515; 4,256,834; and 4,261, 968); enzyme and enzyme inhibitor pairs on different reagents (U.S. Pat. Nos. 4,208,479; 4,233, 401; 3,817,837; and European patent EP 165716); latex turbidometric inhibition assays (Price and Newman, "Light Scattering Immunoassay," Principles and Practice of Immunoassay, (Price and Newman, eds.) New York: Stockton Press, 1991, pages 445-481); chromophore and chromophore modifier pairs on different reagents (U.S. Pat. No. 4,208,479); and cloned enzyme donor immunoassays.

Useful labels for use in the analogs of this invention for immunoassay techniques include but are not limited to radioisotopes, a fluorescent group, a fluorescence quenching group, a phosphorescent group, a chemiluminescent group, an electrochemically active group, an electrochemiluminescent group, any group that undergoes a change in fluorescence, phosphorescence, chemiluminescence or electrochemical property upon binding, an enzyme, an enzyme donor, an enzyme inhibitor, an enzyme substrate, an enzyme cofactor, and an enzyme prosthetic group.

Assays of this invention include both sandwich and competition assays. Sandwich assays typically involve forming a complex in which the analyte to be measured is sandwiched between one reagent, such as a first antibody used ultimately for separation of the complex, and another reagent, such as a second antibody used as a marker for the separated complex. Competition assays involve a system in which the analyte to be measured competes with an analog of the analyte for binding to another reagent, such as an antibody. CEDIA® is an example of a competition assay. The invention also embodies assays that are neither sandwich nor competition assays, as in certain assays involving immunoprecipitation.

Immunoassays specific for ecstasy-class compounds using anti-ecstasy-class-compound antibodies of this invention are rendered specific by virtue of the specificity of the antibody. For assays further employing protein conjugates, such as when a hapten (i.e., an ecstasy-class compound or an analog) is labeled with an enzyme polypeptide, the hapten can be attached to the protein conjugate by any suitable method. In certain embodiments, the chemistry described herein for formation of immunogenic protein conjugates of analogs is also used to prepare the protein conjugate used as an assay reagent. In this way, the hapten core is presented to the antibody in about the same orientation as during the immunization event when the antibody was generated.

Assay methods of this invention include homogeneous enzyme assays in which an ecstasy-class compound or an analog is conjugated to an active enzyme. The conjugation is arranged so that the binding of an anti-ecstasy-class-compound antibody to the analog affects enzymatic activity in a quantitative fashion. If a sample containing an ecstasy-class compound is premixed with the antibody, the antibody will complex with the ecstasy-class compound and be prevented from binding to the enzyme conjugate. In this way, the activity of the enzyme can be correlated with the amount of an ecstasy-class compound present in the sample. Enzyme amplification assays are reported in U.S. Pat. No. 3,852,157.

Enzyme complementation assays are generally described in U.S. Pat. No. 4,708,929. Related reagents and methods are taught in U.S. Pat. Nos. 5,254,577; 5,444,161; 5,464, 747; and 5,514,560. Cloned enzyme donor immunoassays for procainamide and N-acetylprocainamide (NAPA) are described in U.S. Pat. Nos. 5,439,798 and 5,525,474. For the purposes of patent prosecution in the U.S., the aforelisted patents are hereby incorporated herein in their entirety by reference. Enzyme complementation assays based on the enzyme beta-galactosidase are readily available commercially under the registered trademark CEDIA®. The reader is referred to CEDIA® product inserts and technical manuals for further information.

Typically, an enzyme complementation immunoassay of this invention involves combining the sample with: an ecstasy-class-compound-specific antibody; an enzyme donor polypeptide conjugate; an enzyme acceptor polypeptide (wherein the enzyme acceptor polypeptide is capable of forming with said enzyme donor polypeptide conjugate an active enzyme complex in the absence of an antibody to ecstasy-class compounds), and a substrate capable of being transformed by the active enzyme complex into a product. The amount of product is then measured, usually as a function of time.

For complementation assay purposes, the ecstasy-class-compound-specific antibody advantageously may be an antibody raised against an analog/protein conjugate of this invention, or having the characteristics of such an antibody. Besides being screened for cross-reactivity, desirable antibodies have three other features. One, referred to as "inhibition", relates to how well the antibody binds the enzyme-donor conjugate and blocks (inhibits) formation of active beta-galactosidase. Sufficient inhibition (preferably at least about 70%) is needed in order to provide an adequate signal. A second criterion is the titer of the antibody required to obtain the desired level of inhibition, with inhibition at lower antibody levels being desirable. A third criterion, referred to as "modulation", relates to how well the sample analyte is able to compete with the conjugate for enzyme binding. Modulation is calculated as the difference in enzyme rate between a sample having a given analyte concentration and a sample having no analyte, divided by the rate at the given analyte concentration. Better modulation at the target concentration for the positive/negative decision point (i.e., the assay "cut-off") correlates with better assay sensitivity and precision at concentrations near the cut-off.

The enzyme-donor enzyme-acceptor pair is a pair of polypeptides which spontaneously assemble in reagent buffer to form an active enzyme complex. The active enzyme complex is capable of enzymatically transforming a substrate into a product that is differentially detectable. Typically, the product is a different color from the substrate and can be quantified in a spectrophotometer. The donor and acceptor pair are typically two functional subunits of a common enzyme. The subunits may be noncovalently associated in the native enzyme, or they may be defective versions of a common polypeptide that complement each other when together.

If desired, enzyme-donor and enzyme-acceptor polypeptides may be based on the enzyme beta-galactosidase polypeptide. A "beta-galactosidase polypeptide" is a polypeptide identifiable on the basis of its amino acid sequence or enzymatic activity as being developed from an enzyme with beta-galactosidase activity. The definition encompasses not only naturally occurring beta-galactosidase, but also fragments, deletion mutants, fusion proteins, mutants and other variants based thereupon obtained by such processes as enzymatic fragmentation and genetic engineering of relevant encoding sequences. Particular beta-galactosidase polypeptides are described in the aforelisted U.S. Patent applications pertaining to cloned enzyme donor immunoassays.

Beta-galactosidase enzyme acceptors may be produced by a deletion mutant of the beta-galactosidase gene. EA22, for example, has a deletion of amino acid residues 13–40. Other enzyme acceptor fragments of beta-galactosidase which contain the natural sequence which includes amino acid position 602 may also be used. Other examples include EA5, 3A11, EA14, EA17, EA18, EA20, EA23 and EA 24. The distal end of the deleted segment normally falls between amino acid positions 26 and 54 of the beta-galactosidase sequence. In EA22, the distal end of the deletion segment is amino acid 40. Another beta-galactosidase enzyme donor is ED28. ED28 is a 90 amino acid peptide containing residues 6–45 of beta-galactosidase, with cysteines at positions 1 and 46 (relative to the numbering of the original beta-galactosidase fragment). The sequence of ED28 is (SEQ ID NO.1) Met-Asp-Pro-Ser-Gly-Asn-Pro-Tyr-Gly-lle-Asp-Pro-Thr-Gln-Ser-Ser-Pro-Gly-Asn-lle-Asp-Pro-Cys-Ala-Ser-Ser-Asn-Ser-Leu-Ala-Val-Val-Leu-Gln-Arg-Arg-Asp-Trp-Glu-Asn-Pro-Gly-Val-Thr-Gln-Leu-Asn-Arg-Leu-Ala-Ala-His-Pro-Pro-Phe-Ala-Ser-Trp-Arg-Asn-Ser-Glu-Glu-Ala-Arg-Thr-Asp-Cys-Pro-Ser-Gln-Gln-Leu-Ala-Gln-Pro-Glu-Trp-Gly-Leu-Glu-Ser-Arg-Ser-Ala-Gly-Met-Pro-Leu-Glu; see also European Patent Application Nol. 90308937.3 and U.S. Pat. Nos. 4,708,929; 5,444,161; and 5,763,196. The two cysteine residues can be used for exact and reproducible placement of sulfhydryl-reactive adducts of an ecstasy-class compound or analog as described earlier. Before conjugation with the hapten, reducing reagent that is generally used in the storage of ED28 is removed by a suitable desalting technique, such as on a Pharmacia NAP5™ column as described in U.S. Pat. No. 5,439,798. The ecstasy-class compound or analog is then conjugated with the maleimide adducts as described elsewhere in this disclosure. Adjustment of the linkage can be performed by monitoring enzyme inhibition by an ecstasy-class-compound-specific antibody. Typical linker groups used are maleimide adducts, where the maleimide nitrogen and the ecstasy-class-compound nitrogen or analog nitrogen are linked by —$(CH_2CH_2)$—

Exemplary substrates for use in immunoassays based on beta-galactosidase include those described in U.S. Pat. Nos. 5,032,503; 5,254,677; 5,444,161; and 5,514,560. One such substrate is chlorophenolred-beta-D-galactopyranoside. Optimization of the features and conditions of the assays embodied by this invention is a matter of routine experimentation within the skill of the ordinary artisan.

Reagents and buffers used in the assays of this invention can be packaged separately or in combination into kit form to facilitate distribution. The reagents are provided in suitable containers, and typically provided in a package along with written instructions relating to assay procedures.

The analogs and the specific antibodies of this invention can be insolubilized by attachment to a solid capture vehicle. This can be, for example, a vessel wall, to a particulate, or to a large molecular weight carrier that can be kept in suspension but is removable by physicochemical means, such as centrifugation or microfiltration. The attachment need not be covalent, but is at least of sufficient permanence to withstand any separation techniques (including washes) that are part of the assay procedure. Suitable particulate materials include agarose, polystyrene, cellulose, polyacrylamide, latex particles, magnetic particles, and fixed red cells. Suitable commercially available matrices include Sepharose® (Pharmacia), Poros® resins (Roche Molecular Biochemicals, Indianapolis), Actigel Superflow™ resins (Sterogene Bioseparations Inc., Carlsbad Calif.), and Dynabeads™ (Dynal Inc., Lake Success, N.Y.). The choice is not critical, and will generally depend on such features as stability, capacity, accessibility of the coupled antibody, flow rate, the ability to disperse the resin in the reaction mixture, and ease of separation.

Suitable approaches for attaching the substance onto the solid surface will depend on the nature of the analog or antibody, and the solid phase. Attachment systems include those shown in the following table:

TABLE 1

Conjugation Chemistry

| Site of Attachment or Derivatization on Resin | Reagent Used | Site of Attachment of Antibody |
|---|---|---|
| Hydroxyl groups | CNBr | Amino groups |
| Hydroxyl groups | Carbonyldiimidazole | Amino groups |
| Aldehyde groups | $NaBH_4$ or $NaCNBH_3$ | Amino groups |
| Sulfhydryl-reactive group ($RCH_2I$, R-maleimide, disulfide) | (Spontaneous) | Disulfide bonds (after reduction) |
| Amino groups | Water-soluble carbodiimides | Carboxyl groups |
| Carboxyl groups | Water-soluble carbodiimides | Amino groups |
| N-hydroxysuccinimide esters | (Spontaneous) | Amino groups |
| Epoxide groups | (Spontaneous) | Amino groups |
| Hydrazide groups | (Spontaneous) | Carbohydrate groups (after periodate oxidation) |
| Protein A or Protein G | (Spontaneous) | Antibody Fc region |

For example, antibodies purified by chromatography on Protein A affinity chromatography can be attached to cyanogen bromide-activated Sepharose® CL-4B (Pharmacia, Piscataway, N.J.) as recommended by the manufacturer. The resin is prepared to contain approximately 0.8 mg of bound antibody per mL of resin bed volume. The procedure can be conducted as follows: the required amount of activated Sepharose® is weighed, taking into account that 1 g freeze-dried material swells to 3.5 mL gel volume. The gel is reconstituted and washed in wash buffer (1 mM HCl) (3 cycles of resin wash, at 200 mL per gram), and then washed three times with coupling buffer (0.1 M $NaHCO_3$, 0.5 M NaCl, pH 8.3) (50 mL per gram) using a Buchner funnel. The antibody is dissolved or exchanged into coupling buffer, and 5–10 mg are coupled per mL. The gel cake is transferred to a suitably sized container, the antibody is added, and the volume is adjusted to make a 50% slurry. The suspension is mixed end-over-end for 2 h at room temperature, or overnight at 2° C. to 8° C. (stirring is avoided to prevent shearing of the beads). The proportion of antibody successfully coupled can be determined by measuring $A_{280}$ before and after coupling. Blocking buffer is then added (1 M ethanolamine pH 8.0, or 0.2 M Tris buffer, pH 8.0), and the suspension is mixed end-over-end for a further 2 h at room temperature, or overnight at 20 to 8° C. The gel is washed in a Buchner funnel with coupling buffer, second wash buffer (0.1 M acetate, 0.5 M NaCl, pH 4.0), and then coupling buffer 9100 mL each per gram). After final wash with coupling buffer, the resin is made into a 50% (v/v) slurry with phosphate-buffered saline (PBS, pH 7.4, 0.09% sodium azide). The prepared affinity resin can be optionally diluted with a 50% (v/v) slurry of inactivated Sepharose® 4B to yield the desired binding capacity.

Of course, antibodies for insolubilization can be selected according to different criteria than the ones used for assay purposes. Modulation is not, but high capacity (or affinity) and low cross-reactivity with potential interfering substances, such as amphetamine and methamphetamine, is desirable for a solid-phase antibody. An antibody specific for ecstasy-class compounds and suitable for use as an insolubilized antibody has been obtained and has the laboratory designation 1A9.

Insolubilized antigen can be used in assays for antibody, and insolubilized antibody can be used in assays for immunogen. Labeling methods and principles of various types of immunoassay are provided earlier in this disclosure. In a solid phase assay, the test sample is typically mixed with the solid phase to permit binding of any test substance. Then the solid phase is separated from the sample and any unbound material, and the solid phase is washed. The next step is to determine on the solid phase any substance that has bound from the sample. This can be done by including in the reaction mixture a labeled equivalent of the analyte or antibody being tested for, and determining the amount of analyte or antibody by competition. One such method is described in U.S. Pat. No. 4,551,426. Alternatively, the solid phase can be used in a sandwich format, reacting the washed resin with a detecting agent capable of determining any substance which has bound the resin specifically.

Insolubilized antigen and antibody can also be used as affinity resins for the purpose of purifying or enriching substances that bind them. The method comprises incubating the insolubilized antigen or antibody with the source material under conditions permitting the substance to bind, removing the source material, optionally washing the solid phase, and then recovering the bound substance. Materials that bind by way of antigen-antibody reactivity can generally be eluted using organic solvents, high or low pH buffers (such as dilute acetic acid, or glycine buffer, pH 2.4), high salt (such as a buffered solution of 1 M KSCN), or organic solvents (such as methanol).

In a variation of this, insolubilized antigen or antibody can be used to pre-process a sample before testing in an assay system. For example, if a sample tests positive for an ecstasy-class compound, it can be treated with an appropriate amount of anti-ecstasy-class-compound resin and then retested. The test result will be confirmed as positive if the resin succeeds in removing detectable analyte from the resin. Further elaboration of the adsorption method of running a confirmatory test is described in International patent application WO 98/26644.

In another variation, the resin is used, not to eliminate the analyte from the sample, but to enrich for it. One system constitutes a sample extraction kit in the ImmunElute™ product line by Microgenics. An antibody to ecstasy-class compounds with the desired specificity characteristics is coupled to agarose as already described. The resin is provided as a 5 mL suspension (50% v/v) in a suitable buffer containing 0.1% sodium azide as preservative. The kit also contains poly prep columns of 10 mL each having top caps and removal plugs on the bottom outlet below the frit or filter holding the resin in place.

To perform the affinity enrichment, the biological sample is clarified if necessary to remove turbidity, by centrifugation or filtration. Negative control and standards are prepared by providing analyte-free urine, dividing into separate test tubes, and adding known amounts' of analyte over the expected range. The control, standards, and test samples (volumes up to −10 mL) are then layered onto a corresponding extraction column. If appropriate and desired, an internal control can be included in each sample, as long as the controlling substance is also recognized by the antibody and does not interfere with either the extraction or the assay. Certain analogs according to this invention qualify for this purpose. The resin is mixed to provide an even suspension, and 200 µL suspension is added to each sample column. The columns are then capped and mixed on a rocking mixer for 30 to 120 min, then placed on a suitable rack, small-end down. The plug is removed and the column is allowed to drain. The resin is washed (e.g., 10 mL phosphate-buffered saline, followed by 2×10 mL deionized and distilled water. After drying the resin under a light vacuum, the sample is then eluted. To accomplish this, the column is replugged and 10 mL of a suitable eluting solvent such as methanol is pipetted onto the column and allowed to stand for 2–5 min. The plug is then removed and the methanol is eluted from the bottom of the column. The methanol extract can then be tested by a suitable method, such as GC/MS. Alternatively, an aliquot can be diluted in aqueous buffer and tested by immunoassay.

Additional illustration of the development and use of reagents and assays according to this invention are provided in the Example section below. The examples are provided as a further guide to a practitioner of ordinary skill in the art, and are not meant to be limiting in any way.

EXAMPLES

Example 1

Preparation of 3,4-methylenedioxyphenylacetone (3,4-MDPA)

Hydrogen peroxide (70 ml, 30%) was added with caution to a solution of formic acid (350 ml, 88%) in a three-necked flask (1 L) cooled with running water. Isosafrole (72 ml) was added drop-wise, by a dropping funnel, to the reaction mixture at a rate to keep the temperature of the reaction mixture below 35° C. After the complete addition of isosafrole, a non-homogeneous solution was obtained. At this point, acetone (200 ml) was added to the reaction mixture at a rate to keep the temperature below 35° C. The reaction was allowed to stand at room temperature overnight. The solvent was removed by a rotary evaporator equipped with a dry-ice acetone cold trap, a high vacuum pump and a water bath with temperature not exceeding 30° C. Ethyl ether (500 ml) was added to the residue. The solution was transferred into a separatory funnel. The organic phase was washed with sodium bicarbonate (0.1 N, 2×500 ml) and water (3×300 ml). The organic phase was transferred into a round bottom flask. The solvent was removed by rotary evaporation. Concentrated sulfuric acid (75 ml) was diluted drop-wise in water (425 ml). Methanol (160 ml) was added to the oily residue, and mixed to obtain a homogeneous solution. The sulfuric acid solution was added to the methanolic reaction mixture. The flask was equipped with a water-cooled reflux condenser and a heating mantel. The reaction mixture was heated to reflux for 4 hours. The heat was removed and crushed ice (150 g) was added to the reaction mixture. The reaction mixture was transferred into a separatory funnel and extracted with ethyl ether (1×350 ml, 1×150 ml and 1×100 ml). The combined organic layers were washed with water (3×150 ml). Sodium hydroxide (40 ml, 0.1 N) was diluted in water (360 ml). The organic phase was washed with diluted sodium hydroxide (2×200 ml, 10 mM) and saturated sodium chloride solution (100 ml). The organic layer was dried with anhydrous sodium sulfate (20 g) overnight. The drying agent was filtered and the cake was washed with ethyl ether (2×10 ml). The solvent was removed by rotary evaporation. The product was distilled at reduced pressure (2–0.5 mmHg). The second fraction distilling at 90–100° C. (~1 mmHg) contained product. The product was identified by EI/MS with the m/z of 182. Infrared spectrum (cm$^{-1}$) indicated 1714 (C=O) and 2898 (C—H) stretches corresponding to the product.

Example 2

Preparation of 1-N-tert-butoxycarbonyl-1,4-diaminobutane (N-boc-DAB)

Dichloromethane (75 ml) was added to a 250 ml round bottom flask. A dry and clean magnetic stirrer was added to the reaction flask. 1,4-diaminobutane (4.7 g) was added to the reaction flask. The reaction flask was cooled in ice for 15 min. Di-tert-butyldicarbonate (2.75 g) was dissolved in dichloromethane (25 ml), and then transferred into a liquid addition funnel. The di-tert-butyldicarbonate solution was added drop-wise to the reaction over a period of one hour. The reaction mixture was allowed to stir overnight. The reaction mixture was washed with sodium hydroxide (3×50 ml, 0.1 N), water (2×50 ml) and saturated sodium chloride solution (2×25 ml). The product was purified by flash column chromatography on silica gel (solvent: dichloromethane/methanol/ammonium hydroxide; 60/40/3 v/v/v). Major spot with $R_f$=0.3 and positive to ninhydrin spray corresponded to the product. The fractions containing the product were pooled and the solvent was removed. 1.9 g of product was obtained after drying under high vacuum overnight.

Example 3

Preparation of N-(4'-tert-butoxycarbonylaminobutyl)-3,4-methylenedioxyamphetamine (N-boc-AB-MDA)

3,4-MDPA (1.3 g) was dissolved in isopropyl alcohol (1 ml) in a 10 ml round bottom flask. N-boc-DAB (1.5 g) was dissolved in isopropyl alcohol, and added to the reaction mixture. HgCl$_2$ (50 mg) was dissolved in a separate container in absolute ethanol (2 ml). Isopropyl alcohol (7 ml) was added to the HgCl$_2$ solution. The HgCl$_2$ solution was added to the reaction mixture. Aluminum foil (0.9 g) was added in small pieces to the reaction mixture. The reaction was initiated by heating, using a heat gun. Start of the reaction coincided with generation of small hydrogen bubbles. After complete disappearance of the aluminum foil, the reaction was allowed to stand for 30 min. At this point the reaction mixture had a gray slurry appearance. Methanol (25 ml) was added to the reaction mixture. The reaction mixture was first filtered through a coarse filter paper, then over a cake of celite. The solvent was removed by rotary evaporation. A clear oily residue was obtained. Analysis by thin layer chromatography (TLC) on silica gel plates with fluorescent indicator indicated product at $R_f$=0.3 (solvent: dichloromethane/methanol/triethylamine; 93/7/1; v/v/v). The product was purified by flash chromatography. Appropriate fractions were pooled, and the product was isolated as single spot by TLC. The product weighed 1.2 g after drying.

Example 4

Preparation of N-(4'-aminobutyl)-3,4-methylenedioxyamphetamine (AB-MDA)

N-boc-AB-MDA (300 mg) was dissolved in trifluoroacetic acid (2 ml) in an amber glass vial. A magnetic stirrer was added to the reaction mixture. The reaction mixture was stirred for one hour. TFA was removed under reduced pressure. The off-white solid product was stored at −80° C. until further use.

Example 5

Preparation of 4'-maleimidobutyl-3,4-methylenedioxyamphetamine (MB-MDA)

AB-MDA (51 mg) was dissolved in tetrahydrofuran (2.5 ml). Saturated sodium bicarbonate solution (1.5 ml) was added to the reaction mixture. Methoxycarbonylmaleimide (17 mg) was added to the reaction mixture. An appropriately sized magnetic stirrer was added to the reaction mixture. The reaction mixture was stirred for 2 hours. At this point the reaction was complete. Water (15 ml) and ethylacetate (25 ml) were added to the reaction mixture. The mixture was transferred into a separatory funnel. The organic phase was washed with water (10 ml) and saturated sodium chloride solution (15 ml). The organic phase was dried over sodium sulfate (2 g). The solvent was removed by rotary evaporation. The product was purified by HPLC using water and acetonitrile (both containing 0.1% TFA) as mobile phase. A semipreparative C4 column was used as a stationary phase. The main peak ($R_f$=14 min) was collected and lyophilzed. This gave 18.4 mg of the product. Mass Spectrum (EI), m/z 329 (M-1), 315 (M-15), 195 (M-135), $^1$H NMR ($CD_3OD$), δ (ppm), 6.83 (s, 2H, =CH—), 6.69–6.79 (m, 3H, Ar—H), 5.9 (s, 2H, O—$CH_2$—O—), 3.55 (t, 3H, Ar—$CH_2$—), 3.41 (m, 1H N—CH—), 3.06 (m, 4H, N—$CH_2$—), 1.67 (m, 4H, —$CH_2$—), 1.21 (d, 3H, —$CH_3$).

Example 6

Preparation of ED28-(MB-MDA)$_2$ Conjugate

A solution of MB-MDA (0.2 mg) in acetonitrile (HPLC grade, 0.2 ml) was added to a solution of desalted ED28 (1 mg) in sodium phosphate buffer (2.0 ml, 100 mM, pH 7.0). The reaction was allowed to stand for 1 hr at room temperature. The conjugate was purified by HPLC using water and acetonitrile (both containing 0.1% TFA) as mobile phase. A semi-preparative C4 column was used as stationary phase. The conjugate eluted at $R_f$=20.4 min using a step linear gradient of 20 to 40% acetonitrile in 20 min with a run time of 25 min. The flow rate was 4 ml per min. The purification was monitored at 280 nm. The product was quantitated to be 0.9 mg, using $OD_{280}$ and $\epsilon_{280}$=22,600 $cm^{-1}M^{-1}$.

Example 7

Preparation of Ecstasy-Class Immunogen

Keyhole limpet hemocyanin (KLH, 20 mg, Pierce Chemicals) was reconstituted in sodium phosphate buffer (2 ml, 100 mM, pH 8.00). 2-iminothiolane (2-IT, 3.1 mg) was dissolved in HPLC grade water (0.5 ml). The solution of 2-IT was added to the KLH solution in one portion. The reaction mixture was mixed for 1 min to obtain an almost clear gray solution. The reaction was allowed to stand for 60 min. The activated KLH-(SH)$_n$ was desalted on a Sephadex PD-10 column pre-equilibrated with sodium phosphate buffer (100 mM, pH 7.0). The SH loading was determined to be 1390 per KLH molecule (M. Wt. 5,000,000). DMSO (0.6 ml) was added to the KLH-(SH)$_{1390}$ solution. The MB-MDA (2.67 mg) was dissolved in acetonitrile (0.15 ml). The solution of MB-MDA was added to the KLH-(SH)$_{1390}$ solution. The reaction mixture was stirred overnight at 4° C. The immunogen was dialyzed twice with PBS solution (150 mM NaCl, 10 mM sodium phosphate, pH 7.0–7.1) containing DMF (20% v/v), and twice with PBS solution. The dialyzed immunogen solution (~34 ml, ~0.5 mg/ml) was used for immunization of mice.

Example 8

Development of Anti-MDA Polyclonal Antibodies

Mice were immunized by administration of MDA-MB-21T-KLH in a series of injections. Mice were bled ten days after the third immunization. The sera were assayed in 96-well plate version of a beta-galactosidase enzyme complementation assay as follows:

a. Enzyme acceptor (EA) Reagent was prepared by diluting EA protein with CEDIA Buffer. When testing for response to analyte, MDMA was added to the EA Reagent. The components and concentrations used are listed below:

TABLE 2

CEDIA Buffer

| Component | F.W. or Stock | Concentration* |
|---|---|---|
| Potassium Phosphate, dibasic | 174.18 g/mole | 30 mM |
| Potassium Phosphate, monobasic | 136.09 | 30 mM |
| Sodium Chloride | 58.44 g/mole | 400 mM |
| EGTA | 380.35 g/mole | 10 mM |
| Tween 20 | 10% | 0.05% |
| Magnesium Acetate | 214.46 g/mole | 2 mM |
| Sodium Azide | 65.01 g/mole | 0.02% |

TABLE 3

EA Reagent

| Component | F.W. or Stock | Concentration* |
|---|---|---|
| EA-22 | varies | 25 Units/ml |
| MDMA | | 0 or 27.5 ng/mL |
| CEDIA Buffer | | As above | b. Enzyme Donor (ED) Reagent was also prepared in CEDIA Buffer with the components below.

TABLE 4

ED Reagent

| Component | F.W. or Stock | Concentration* |
|---|---|---|
| ED28-(MB-3,4-MDA)$_2$ | | 1 nM |
| CPRG | 116 mg/m. | 0.5 mg/ml |
| Goat anti-Mouse Serum | neat | 0.5% |
| CEDIA Buffer | | As above |

*Concentration indicates final concentration after reconstitution.

c. The assay protocol was as follows: fifty µl diluted antibody was added to a well of a 96-well microtiter plate. Seventy-five µl EA reagent with or without MDMA (27.5 nM; equivalent to a concentration of 1,000 ng/mL in a urine sample) was added to each well and incubated for 15 minutes at room temperature. Then 75 µl ED reagent was added and incubated for 1 hour at room temperature. The absorbance was read at 540 nm with a 690 nm reference wavelength.

d. Data analysis was performed as follows: % inhibition was calculated as the absorbance in the presence of antibody divided by the absorbance in the absence of antibody, times 100%. % modulation was calculated as follows: (absorbance in the presence of antibody and MDMA minus absorbance in the presence of antibody and the absence of MDMA) divided by the absorbance in the presence of antibody and MDMA, times 100%.

After 11 weeks, the mice were bled and the serum assayed for anti-MDA antibodies using MDMA. Results shown in Table A demonstrate binding of the Enzyme Donor-MDA conjugate; maximum inhibition was >80% for all 13 mice, and maximum modulation of 22 to 55% was achieved at titers of 1:400 to 1:1600. Mouse 3C was chosen for hybridoma production based on the finding of maximal response to MDMA in the assay.

TABLE 5

Testing of anti-MDA Polyclonal Antisera using MDMA

| Mouse # | | 1/50 | 1/100 | 1/200 | 1/400 | 1/800 | 1/1600 | 1/3200 | 1/6400 |
|---|---|---|---|---|---|---|---|---|---|
| 1A | % Inhibition | 88 | 88 | 90 | 90 | 86 | 75 | 51 | 30 |
|    | % Modulation | 0 | 4 | 11 | 17 | 26 | 32 | 22 | 18 |
| 2A | % Inhibition | 88 | 88 | 89 | 88 | 81 | 66 | 45 | 25 |
|    | % Modulation | 0 | 4 | 9 | 13 | 23 | 19 | 14 | 6 |
| 3A | % Inhibition | 89 | 88 | 88 | 83 | 70 | 49 | 29 | 14 |
|    | % Modulation | 1 | 8 | 17 | 29 | 26 | 20 | 13 | 6 |
| 4A | % Inhibition | 88 | 89 | 89 | 89 | 84 | 70 | 48 | 28 |
|    | % Modulation | 0 | 0 | 5 | 12 | 23 | 24 | 18 | 10 |
| 1B | % Inhibition | 87 | 88 | 89 | 86 | 75 | 54 | 30 | 16 |
|    | % Modulation | 2 | 6 | 22 | 39 | 38 | 29 | 17 | 11 |
| 2B | % Inhibition | 90 | 91 | 91 | 91 | 88 | 76 | 53 | 32 |
|    | % Modulation | 3 | 14 | 19 | 32 | 41 | 39 | 29 | 15 |
| 3B | % Inhibition | 83 | 84 | 84 | 74 | 55 | 30 | 13 | 6 |
|    | % Modulation | 0 | 5 | 18 | 26 | 21 | 10 | 4 | 5 |
| 4B | % Inhibition | 88 | 89 | 90 | 91 | 91 | 87 | 74 | 52 |
|    | % Modulation | 0 | 0 | 3 | 0 | 9 | 22 | 15 | 10 |
| 1C | % Inhibition | 85 | 87 | 88 | 89 | 87 | 80 | 64 | 41 |
|    | % Modulation | 0 | 3 | 6 | 12 | 21 | 28 | 27 | 17 |
| 2C | % Inhibition | 87 | 88 | 88 | 86 | 77 | 63 | 44 | 22 |
|    | % Modulation | 9 | 14 | 17 | 22 | 24 | 25 | 12 | 8 |
| *3C | % Inhibition | 85 | 87 | 89 | 90 | 87 | 79 | 61 | 42 |
|    | % Modulation | 0 | 3 | 14 | 31 | 46 | 55 | 44 | 31 |
| 4C | % Inhibition | 86 | 88 | 90 | 89 | 84 | 72 | 51 | 28 |
|    | % Modulation | 0 | 0 | 6 | 10 | 20 | 17 | 15 | 6 |
| 5C | % Inhibition | 86 | 86 | 87 | 88 | 83 | 72 | 51 | 31 |
|    | % Modulation | 0 | 0 | 5 | 22 | 29 | 30 | 22 | 14 |

*= Mouse used for first fusion

Example 9

Development and Selection of Anti-MDA Monoclonal Antibodies Using MDMA

The spleen from mouse 3C was harvested and the spleen cells were fused with myeloma cells Using polyethylene glycol as the fusion agent. The parental myeloma used for all fusions was P2X63-Ag8.653, purchased through the American Type Culture Collection (ATCC). The chronology of events for development of monoclonal antibodies raised using KLH-2IT-MB-MDA was as follows:

| | |
|---|---|
| First Immunization | Time 0 |
| Second Immunization | 4 weeks |
| Third Immunization | 8 weeks |
| Mice Bled | 9 weeks |
| Sera from first bleed titered | 11 weeks |
| Fourth Immunization | 22 weeks |
| First fusion performed | 25 weeks |

The first fusion produced 20 clones producing antibody which inhibited enzyme formation by the ED-MDA conjugate in a 96-well CEDIA® style enzyme complementation assay. As shown in Table 6. five of these antibodies gave modulation with MDMA of >20%; the remainder gave modulation of ≦15%. As shown in Table 7, five of these antibodies gave appreciable cross-reactivity to the major MDMA-class drugs MDMA, MDA, MDEA, BDB and MBDB, but little or no cross-reactivity to HMMA (a pharmacologically-inactive analog of MDMA), amphetamine or methamphetamine. The five clones listed in Table 6 were retained for further evaluation, and culture fluid supernatants containing expressed immunoglobulin were prepared for analysis in an automated CEDIA® assay.

TABLE 6

Cell Culture Supernatant Screening Data

| Antibody | | 1:2 | 1:4 | 1:8 | 1:16 | 1:32 | 1:64 | 1:128 | 1:256 | 1:512 | 1:1024 | 1:2048 | 1:4096 |
|---|---|---|---|---|---|---|---|---|---|---|---|---|---|
| 1A9 | % Inhibition | 76 | 78 | 71 | 58 | 42 | 28 | 17 | 11 | 11 | 12 | 7 | 6 |
|     | % Modulation | 11 | 35 | 54 | 49 | 37 | 24 | 14 | 7 | 5 | 9 | 0 | -5 |
| 5B8 | % Inhibition | 84 | 87 | 87 | 83 | 74 | 59 | 40 | 24 | 15 | 7 | 3 | 7 |
|     | % Modulation | -2 | 6 | 11 | 17 | 21 | 18 | 9 | 5 | -1 | 0 | -1 | -3 |
| 5C2 | % Inhibition | 85 | 82 | 72 | 58 | 38 | 24 | 11 | 6 | 5 | 5 | 3 | 10 |
|     | % Modulation | 62 | 71 | 66 | 54 | 35 | 23 | 10 | 6 | 2 | 0 | 2 | 1 |

TABLE 6-continued

Cell Culture Supernatant Screening Data

| Antibody | | Dilution | | | | | | | | | | | |
|---|---|---|---|---|---|---|---|---|---|---|---|---|---|
| | | 1:2 | 1:4 | 1:8 | 1:16 | 1:32 | 1:64 | 1:128 | 1:256 | 1:512 | 1:1024 | 1:2048 | 1:4096 |
| 6G2 | % Inhibition | 85 | 90 | 91 | 90 | 85 | 76 | 61 | 44 | 31 | 18 | 11 | 10 |
| | % Modulation | 2 | 10 | 36 | 68 | 71 | 63 | 50 | 34 | 22 | 10 | 4 | 2 |
| 9F11 | % Inhibition | 85 | 87 | 86 | 82 | 73 | 58 | 41 | 27 | 20 | 17 | 9 | 9 |
| | % Modulation | 1 | 10 | 15 | 19 | 19 | 13 | 8 | 4 | 4 | 5 | −1 | −2 |

TABLE 7

Cross-reactivity of anti-MDA Monoclonal Antibodies in 96-well Microtiter Plate Format

| Isotype | Antibody | MDMA | BDB | HMMA | MDA | MDEA | MBDB | Amphetamine | Metham-phetamine | % Mod. |
|---|---|---|---|---|---|---|---|---|---|---|
| $IgG_1$, K | 1A9 | 100 | 25 | <0.1 | 40 | 153 | 15 | <0.1 | <0.1 | 54 |
| $IgG_1$, K | 5B8 | 100 | 11 | <0.4 | 23 | 1648 | 23 | 6 | 21 | 21 |
| $IgG_1$, K | 5C2 | 100 | 14 | <0.1 | 44 | 170 | 13 | <0.1 | <0.1 | 72 |
| $IgG_1$, K | 6G2 | 100 | 4 | 0.6 | 3 | 291 | 27 | <0.2 | <7 | 74 |
| $IgG_1$, K | 9F11 | 100 | 11 | <0.8 | 27 | 1719 | 24 | 4 | 17 | 27 |

Example 10

Example of Cedia® Ecstasy-class Assay Performed Using A Hitachi Clinical Chemistry Analyzer a. Preparation of Reagents:

TABLE 8

Lyophilized Enzyme Acceptor Reagent

| Component | F.W. or Stock | Concentration* |
|---|---|---|
| Potassium Phosphate, dibasic | 174.18 g/mole | 10 mM |
| Potassium Phosphate, monobasic | 136.09 g/mole | 10 mM |
| Mannitol | 182.17 | 300 mM |
| Tween 20 | 10% | 0.01% |
| Glutathione | 307.30 g/mole | 0.5 mM |
| Sodium Azide | 65.01 g/mole | 9 mM |
| EA 22 Protein | ~25–30% protein by weight | 1.713 g protein/L |

TABLE 9

Enzyme Acceptor Reconstitution Buffer

| Component | F.W. or Stock | Concentration* |
|---|---|---|
| PIPES | 302.26 | 100 mM |
| Sodium Chloride | 58.44 g/mole | 400 mM |
| EGTA | 380.35 g/mole | 10 mM |
| Magnesium Acetate | 214.46 g/mole | 10 mM |
| Fetal Bovine Serum | Neat | 0.5% |
| Sodium Azide | 65.01 | 20 mM |
| Anti-MDA MAb (1A9) | | |

Working Enzyme Acceptor (EA) reagent was prepared by reconstitution of the lyophilized EA Reagent with EA Reconstitution Buffer according to the concentrations shown above.
*Indicates final concentration after reconstitution.

Enzyme Donor (ED) Reagent was prepared as a liquid reagent with the components below:

TABLE 10

Enzyme Donor Reagent

| Component | F.W. or Stock | Concentration* |
|---|---|---|
| PIPES | 302.36 | 100 mM |
| Sodium Chloride | 58.44 g/mole | 400 mM |
| EGTA | 380.35 g/mole | 10 mM |
| EDTA | | 1 mM |
| Goat Anti-Mouse Serum | Neat | 2.0% |
| CPRG | ~120 mg/ml | 1.6 mg/ml |
| Fragmented BSA | ~38 mg/ml | 2 mg/ml |
| Sodium Azide | 65.01 g/mole | 20 mM |
| ED28-(MB-MDA)$_2$ | | 2 nM |

Both reagents had a pH of 6.9.

b. Assay Protocol: The assay was performed on a Hitachi clinical chemistry analyzer as follows: Sample was pipetted into a reaction cuvette. EA reagent, containing antibody, was added. The mixture was incubated at 37° C. for approximately 5 minutes. ED reagent containing anti-MDA monoclonal substrate was subsequently added, and the incubation continued for 4 minutes at 37° C. The rate of substrate hydrolysis was measured photometrically at 570 nm (with subtraction of background at 660 nm) from four to five minutes after ED addition. The following table summarizes the assay protocol:

TABLE 11

Automated Assay Protocol

| Parameter | Value |
|---|---|
| Sample dispense | 3 µL |
| EA Reagent (R1) | 130 µL |
| Incubation | ~300 sec. |
| ED Reagent (R2) | 130 µL |
| Incubation | ~240 sec |
| Read Frame | ~240–300 sec. after R2 (FD Reagent) addition |
| Wavelength | 660/570 (2°.1°) | c. Results

The Figure shows an ecstasy-class compound standard curve formulated based on data derived using the 1A9 antibody as described above. Table 12 shows cross-reactivity of several ecstasy-class drugs, as well as HMMA, amphetamine and methamphetamine. As seen in the Table, antibody 1A9 is able to detect numerous ecstasy-class compounds in a homogeneous immunoassay based on the CEDIA® technology. Sensitivity of detection (i.e., % modulation) is acceptable, with excellent dose-response at an analyte concentration of 300 ng/mL. The ecstasy-class compounds detected have cross-reactivities as summarized below:

| Compound | Cross-reactivity |
| --- | --- |
| MDMA | 100% |
| MDA | 55% |
| MDEA | 155% |
| MBDB | 23% |
| BDB | 33% |

Advantageously, the CEDIA® ecstasy-class MDMA assay detected neither the pharmacologically-inactive compound HMMA, nor the active compounds amphetamine and methamphetamine.

TABLE 12

MDMA Antibody Specificity

| Compound | Concentration ng/mL | Rate MAU/min | Apparent Dose ng/mL | Cross-Reactivity % |
| --- | --- | --- | --- | --- |
| Antibody 1A9, Experiment 1 | | | | |
| MDMA | 0 | 81 | | |
|  | 300 | 349 | | |
|  | 1000 | 762 | | |
|  | 5000 | 845 | | |
| MDEA | 300 | 446 | 460* | 155* |
|  | 1000 | 842 | 4840 | 484 |
|  | 5000 | 860 | >5000 | |
| MDA | 300 | 228 | 160 | 55 |
|  | 1000 | 573 | 680 | 68* |
|  | 5000 | 807 | 3160 | 63 |
| MBDB | 300 | 143 | 70 | 23 |
|  | 1000 | 341 | 290 | 29* |
|  | 5000 | 695 | 890 | 18 |
| BDB | 300 | 169 | 100 | 33 |
|  | 1000 | 465 | 500* | 50* |
|  | 5000 | 772 | 1490 | 30 |
| HMMA | 300 | 80 | 0 | <0.1 |
|  | 1000 | | | <0.1 |
|  | 5000 | | | <0.1 |
| Antibody 1A9, Experiment 2 | | | | |
| MDMA | 0 | 160.6 | | |
|  | 300 | 378.6 | | |
|  | 1000 | 840.3 | | |
|  | 5000 | 990.8 | | |
| pseudoephedrine | 600,000 | 166.6 | 10 | 0.0017 |
| (±)ephedrine | 1,000,000 | 189.7 | 47 | 0.0047 |
| phenylpropanolamine | 1,000,000 | 185.8 | 41 | 0.0041 |
| Amphetamine | 700,000 | 430.7 | 350 | 0.050 |
| Methamphetamine | 600,000 | 417.4 | 337 | 0.056 |

*best estimate (value within linear range of standard curve)
BDB = 3,4,methylenedioxyphenyl-2-butaneamine
*HMMA 4-hydroxy-3-methoxy methamphetamine Example 11

Enhancement of Cross-reactivity to Eecstasy-class Drugs in the CEDIA® DAU Amphetamines Assay Through the Addition of the 1A9 Anti-ecstasy Antibody and ED-MDA Conjugate The CEDIA® DAU Amphetamines assay was enhanced for its cross-reactivity with the ecstasy drugs MDA, MDMA, MDEA, BDB and MBDB through the addition of the 1A9 anti-ecstasy antibody and ED28-(MB-MDA)$_2$ conjugate. CEDIA® DAU Amphetamines Assay kits were obtained from Microgenics Corporation, Fremont Calif. The kits were reconstituted and were run according to direction for a 500 ng/mL cutoff assay on the Hitachi 911 analyzer. Methamphetamines were used for the cutoff calibrator.

A direct comparison of the CEDIA® DAU Amphetamines assay and the enhanced version was performed. The reagents used were as follows:

Standard CEDIA® DAU Amphetamines Assay

R1: CEDIA® DAU Amphetamines EA Reagent was reconstituted in CEDIA® DAU Amphetamines EA Reconstitution Buffer R2: CEDIA® DAU Amphetamines EA Reagent was reconstituted in CEDIA® DAU Amphetamines ED Reconstitution Buffer Enhanced CEDIA® DAU Amphetamines Assay R1: CEDIA® DAU Amphetamines EA Reagent was reconstituted in CEDIA® DAU Amphetamines ED Reconstitution Buffer, and then MAb 1A9 ascites fluid was added to a final dilution of 1:1200.

R2: CEDIA® DAU Amphetamines ED Reagent was reconstituted in CEDIA® DAU Amphetamines ED Reconstitution Buffer, and then ED28-(MB-MDA)$_2$ was added to a final concentration of 1 nM.

The assay protocol for both reagent sets is shown in table 1:

TABLE 13

Automated Assay Protocol

| Parameter | Value |
| --- | --- |
| Sample dispense | 6 μL |
| EA Reagent (R1) | 130 μL |
| Incubation | ~300 sec. |
| ED Reagent (R2) | 130 μL |
| Incubation | ~240 sec |
| Read Frame | ~240–300 sec. after R2 (FD Reagent) addition |
| Wavelength | 660/570 (2°.1°) |

Results

The amounts of Monoclonal Antibody 1A9 and ED-MDA conjugate added to the enhanced CEDIA® DAU Amphetamines assay were optimized to give approximately the same response to 500 ng/mL of MDA as to 500 ng/mL of methamphetamine. Standard curves for MDA and methamphetamine in the regular and enhanced assays are shown in Table 14.

TABLE 14

Standard curves of normal and enhanced CEDIA ® DAU Amphetamines Assays

| Sample | ng/mL | Standard CEDIA ® Amphetamines Mean Rates mAU/min | Enhanced CEDIA ® Amphetamines Mean Rates mAU/min |
|---|---|---|---|
| Methamphetamine | 0 | 153.6 | 202.2 |
|  | 150 | 187.2 | 233.7 |
|  | 300 | 223.4 | 271.4 |
|  | 500 | 262.3 | 308.3 |
|  | 700 | 289.9 | 334.6 |
|  | 1000 | 320.9 | 360.8 |
| MDA | 0 | 155.6 | 202.2 |
|  | 150 | 155.6 | 228.4 |
|  | 300 | 156.7 | 257.3 |
|  | 500 | 157.9 | 300.3 |
|  | 700 | 159.1 | 343.1 |
|  | 1000 | 160.7 | 388.0 |

Cross-reactivity for methamphetamine and the ecstasy-class drugs in the standard and enhanced CEDIA® DAU Amphetamines assays are shown in Table 15. In all cases there is an improvement in the recognition of the ecstasy-class drugs in the enhanced assay system. Thus addition of antibody to the MDP derivative and labeled MDP analog increased the ability of a conventional amphetamines class assay to detect a broad range of designer amphetamines.

TABLE 15

Cross-reactivities of the Standard and Enhanced CEDIA CEDIA ® DAU Amphetamines Assays

| Compound | Concentration ng/ml | Standard CEDIA ® Amphetamines | Enhanced CEDIA ® Amphetamines |
|---|---|---|---|
| Methamphetamine | 300 | 100 | 100 |
|  | 500 | 100 | 100 |
| MDA | 300 | 5 | 81 |
|  | 500 | 4 | 91 |
| MDMA | 300 | 49 | 129 |
|  | 500 | 50 | * |
| MDEA | 300 | 22 | 153 |
|  | 500 | 21 | * |
| MBDB | 300 | 64 | 80 |
|  | 500 | 73 | 97 |
| BDB | 300 | 5 | 105 |
|  | 500 | 7 | 125 |

*Not determined; above assay range

Various changes, modifications, or alterations may be made to the aspects of the invention described in detail above, without departing from the spirit of the invention or the scope of the following claims.

What is claimed is:

1. An antibody produced from a compound having a structure

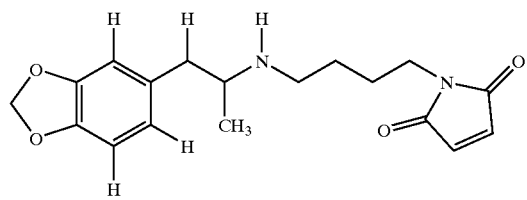

said compound reacted with an immunogenic carrier to produce an immunogen, said antibody capable of preferentially binding to an ecstasy-class compound with a cross-reactivity of less than 10% with each of ephedrine, pseudoephedrine, and phenylpropanolamine and less than 1% with each of amphetamine, methamphetamine, and 4-hydroxy-3-methoxymethamphetamine (HMMA).

2. The antibody of claim 1 further comprising a detectable label.

3. The antibody of claim 1 wherein the immunogenic carrier is chosen from at least one of keyhole limpet hemocyanine and bovine serum albumin.

4. A monoclonal antibody produced from a compound having a structure

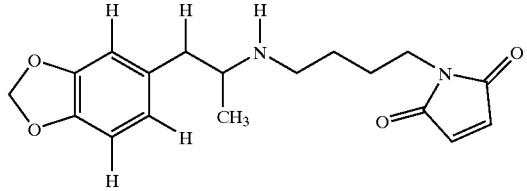

said compound reacted with an immunogenic carrier to produce an immunogen, said antibody capable of preferentially binding to an ecstasy-class compound with a cross-reactivity of less than 10% with each of ephedrine, pseudoephedrine, and phenylpropanolamine and less than 1% with each of amphetamine, methamphetamine, and 4-hydroxy-3-methoxymethamphetamine (HMMA).

5. The monoclonal antibody of claim 4 further comprising a detectable label.

6. The monoclonal antibody of claim 4 wherein the immunogenic carrier is chosen from at least one of keyhole limpet hemocyanine and bovine serum albumin.

7. A method of preferentially detecting at least one ecstasy class compound or analog in a sample comprising mixing the sample with a monoclonal antibody produced from a compound having a structure

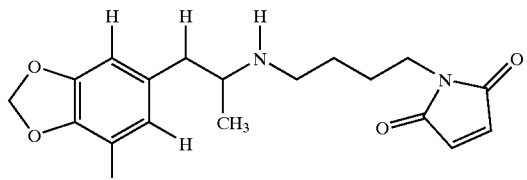

said compound reacted with an immunogenic carrier to produce an immunogen, said antibody capable of preferentially binding to an ecstasy-class compound with a cross-reactivity of less than 10% with each of ephedrine, pseudoephedrine, and phenylpropanolamine and less than 1% with each of amphetamine, methamphetamine, and 4-hydroxy-3-methoxymethamphetamine (HMMA), and a detectable label attached to one of: i) said monoclonal antibody ii) said ecstasy-class analog under conditions that permit preferential binding of the ecstasy-class compound with the antibody, and measuring the detectable label as an indicator of the presence, absence or concentration of said ecstasy-class compound in the sample.

8. The method of claim 7 wherein the sample is premixed with the antibody to inhibit binding of the antibody to an enzyme conjugate in the presence of an ecstasy class compound in the sample.

9. The method of claim 7 wherein assay measuring is by at least one of a sandwich assay, a competitive assay, an enzyme amplification assay, an enzyme complementation assay, a separation based assay, a homogeneous assay, a qualitative assay, and a quantitative assay.

* * * * *

UNITED STATES PATENT AND TRADEMARK OFFICE
CERTIFICATE OF CORRECTION

PATENT NO. : 6,946,547 B2
APPLICATION NO. : 10/457314
DATED : September 20, 2005
INVENTOR(S) : Ria Rouhani et al.

It is certified that error appears in the above-identified patent and that said Letters Patent is hereby corrected as shown below:

Page 1, OTHER PUBLICATIONS, Column 1, reads "Amaiz et al., *Preparation of N-hetercyclic derivatives as...*" and should read -- Arnaiz et al., *Preparation of N-hetercyclic derivatives as...* --.

Page 1, OTHER PUBLICATIONS, Column 2, reads "Belke, J. et al., *Immunoaffinity extraction of morphine,...*" and should read -- Beike, J. et al. *Immunoaffinity extraction of morphine,...* --.

Page 1, OTHER PUBLICATIONS, Column 2, reads "Boehringer Mannheim, *Oplate-Qualitative*, Boehringer,..." and should read -- Boehringer Mannheim, *Opiate-Qualitative*, Boehringer,... --.

Page 2, OTHER PUBLICATIONS, Column 1, reads "Granquist, Lamont #8 *Arladne: 4C-DOM; BL-3912:...*" and should read -- Granquist, Lamont #8 *Ariadne; 4C-DOM; BL-3912:...* --.

Page 3, OTHER PUBLICATIONS, Column 1, reads, "Ruangyutikam, Weraman et al., *Comparison of Three Commercial...*" and should read -- Ruangyuttikarn, Werawan et al., *Comparison of Three Commercial...* --.

Column 4, lines 24-25 read, "...complementation as a measure of ecstasy-class compound (s) in the sample." and should read -- ...complementation as a measure of ecstasy-class compound(s) in the sample. --.

Column 11, line 56 reads, "...radioisotopes such as $^{125}$I enzymes such as peroxides and..." and should read --...radioisotopes such as $^{125}$I, enzymes such as peroxides and --.

Column 14, line 38 reads, "...gen or analog nitrogen are linked by —($CH_2CH_2$)—" and should read -- ... gen or analog nitrogen are linked by - —($CH_2CH_2$)—. -- (*missing end period*)

Column 15, Table 1, line 18 reads, "$RCH_2$l, R-maleimide," and should read -- ($RCH_2$I, R-maleimide,--.

Column 15, line 53 reads, "...temperature, or overnight at 20 to 8°C." and should read --...temperature, or overnight at 2° to 8°C. --.

Column 16, line 58 reads, "...test tubes and adding known amounts' of analyte over..." and should read, -- ...test tubes and adding know amounts of analyte over...--.

UNITED STATES PATENT AND TRADEMARK OFFICE
CERTIFICATE OF CORRECTION

PATENT NO. : 6,946,547 B2
APPLICATION NO. : 10/457314
DATED : September 20, 2005
INVENTOR(S) : Ria Rouhani et al.

It is certified that error appears in the above-identified patent and that said Letters Patent is hereby corrected as shown below:

Column 16, line 60 reads, "…(volumes up to -- 10 mL)…" and should read -- …(volumes up to ~ 10L)… --.

Column 17, line 64 reads, "…tained product. The product was identified by El/MS with…" and should read -- …tained product. The product was identified by EI/MS with… -.

Column 19, line 14 reads, "The main peak ($R_f$=14 min)… and should read -- The main peak ($R_t$ = 14 min)… --.

Column 19, line 15 reads, "This gave 18.4 mg of the product. Mass Spectrum (El), m/z…" and should read -- This gave 18.4 mg of the product. Mass Spectrum (EI), m/z… --.

Column 19, line 19 reads, "…(m, 1H N–CH–)…" and should read --…(m, 1H, N–CH–)… --.

Column 19, line 32 reads, "...phase. The conjugate eluted at $R_f$ = 20.4 min…" and should read --… phase. The conjugate eluted at $R_t$ = 20.4 min…--.

Column 19, lines 66-67 reads, "Mice were immunized by administration of MDA-MB-21T-KLH…" and should read -- Mice were immunized by administration of MDA-MB-2IT-KLH…--.

Column 20, line 63 reads, "...Table A demonstrate binding of the Enzyme Donor-MDA…" and should read --...Table 5 demonstrate binding of the Enzyme Donor-MDA… --

Column 20, line 64 reads, "...conjugate; maximum inhibition was >80% for all 13 mice, …" and should read --… conjugate; maximum inhibition was >80% for all mice,… --

Column 21, line 39 reads, "...cells were fused with myeloma cells Using…" and should read --...cells were fused with myeloma cells using…--.

UNITED STATES PATENT AND TRADEMARK OFFICE
CERTIFICATE OF CORRECTION

| | |
|---|---|
| PATENT NO. | : 6,946,547 B2 |
| APPLICATION NO. | : 10/457314 |
| DATED | : September 20, 2005 |
| INVENTOR(S) | : Ria Rouhani et al. |

It is certified that error appears in the above-identified patent and that said Letters Patent is hereby corrected as shown below:

Column 26, line 4 reads, "Enhancement of Cross-reactivity to Eecstsy-class…" and should read --… Enhancement of Cross-reactivity to Ecstasy-class…. --.

Signed and Sealed this

Twenty-fourth Day of October, 2006

JON W. DUDAS
*Director of the United States Patent and Trademark Office*